(12) United States Patent
Feinstein et al.

(10) Patent No.: US 8,785,408 B2
(45) Date of Patent: Jul. 22, 2014

(54) COMPOSITIONS AND METHODS FOR REDUCING OR PROTECTING AGAINST DELAYED GRAFT FUNCTION (DGF)

(75) Inventors: Elena Feinstein, Rehovot (IL); Shai Erlich, Belmont, CA (US)

(73) Assignee: Quark Pharmaceuticals, Inc., Fremont, CA (US)

( * ) Notice: Subject to any disclaimer, the term of this patent is extended or adjusted under 35 U.S.C. 154(b) by 275 days.

(21) Appl. No.: 12/452,321

(22) PCT Filed: Jun. 26, 2008

(86) PCT No.: PCT/IL2008/000874
§ 371 (c)(1), (2), (4) Date: May 6, 2010

(87) PCT Pub. No.: WO2009/001359
PCT Pub. Date: Dec. 31, 2008

(65) Prior Publication Data
US 2010/0222409 A1 Sep. 2, 2010

Related U.S. Application Data

(60) Provisional application No. 60/964,325, filed on Aug. 10, 2007, provisional application No. 60/937,318, filed on Jun. 27, 2007.

(51) Int. Cl.
*A61K 48/00* (2006.01)
*C07H 21/02* (2006.01)
*C07H 21/04* (2006.01)

(52) U.S. Cl.
USPC .......................... 514/44; 536/23.1; 536/24.5

(58) Field of Classification Search
None
See application file for complete search history.

(56) References Cited

U.S. PATENT DOCUMENTS

| | | | |
|---|---|---|---|
| 4,497,817 A | 2/1985 | Murase et al. | |
| 5,849,774 A | 12/1998 | Jackson et al. | |
| 5,898,031 A | 4/1999 | Crooke | |
| 6,107,094 A | 8/2000 | Crooke | |
| 6,372,249 B1 | 4/2002 | Smith et al. | |
| 6,506,559 B1 | 1/2003 | Fire et al. | |
| 6,593,353 B1 | 7/2003 | Gudkov et al. | |
| 6,982,277 B2 | 1/2006 | Gudkov et al. | |
| 7,008,956 B2 | 3/2006 | Gudkov et al. | |
| 7,012,087 B2 | 3/2006 | Gudkov et al. | |
| 7,056,704 B2 | 6/2006 | Tuschl | |
| 7,078,196 B2 | 7/2006 | Tuschl | |
| 7,432,249 B2 | 10/2008 | Crooke | |
| 7,432,250 B2 | 10/2008 | Crooke | |
| 7,452,987 B2 | 11/2008 | Giese | |
| 7,459,547 B2 | 12/2008 | Zamore | |
| 7,629,321 B2 | 12/2009 | Crooke | |
| 7,781,575 B2 | 8/2010 | Khvorova et al. | |
| 7,825,099 B2 | 11/2010 | Feinstein | |
| 7,842,674 B2 | 11/2010 | Feinstein et al. | |
| 7,893,245 B2 | 2/2011 | Giese | |
| 7,910,566 B2 | 3/2011 | Feinstein | |
| 8,148,342 B2 | 4/2012 | Feinstein et al. | |
| 2002/0006941 A1 | 1/2002 | Gudkov et al. | |
| 2002/0019425 A1 | 2/2002 | Gudkov et al. | |
| 2003/0144331 A1 | 7/2003 | Gudkov et al. | |
| 2003/0176318 A1 | 9/2003 | Gudkov et al. | |
| 2004/0014956 A1 | 1/2004 | Woolf et al. | |
| 2004/0180351 A1 | 9/2004 | Giese et al. | |
| 2004/0209832 A1 | 10/2004 | McSwiggen et al. | |
| 2005/0080246 A1 | 4/2005 | Allerson et al. | |
| 2005/0153337 A1 | 7/2005 | Manoharan | |
| 2005/0222224 A1 | 10/2005 | Gudkov et al. | |
| 2005/0255487 A1 | 11/2005 | Khvorova et al. | |
| 2005/0260620 A1 | 11/2005 | Christiano et al. | |
| 2005/0261191 A1 | 11/2005 | Barasch et al. | |
| 2006/0024278 A1 | 2/2006 | Chen | |
| 2006/0069056 A1 | 3/2006 | Feinstein et al. | |
| 2006/0217329 A1 | 9/2006 | Feinstein | |
| 2007/0031844 A1 | 2/2007 | Khvorova et al. | |
| 2007/0185047 A1 | 8/2007 | Bhat et al. | |
| 2007/0212330 A1 | 9/2007 | Vlodavsky et al. | |
| 2008/0064650 A1 | 3/2008 | Feinstein et al. | |
| 2008/0084471 A1 | 4/2008 | Feinstein et al. | |
| 2008/0108583 A1 | 5/2008 | Feinstein et al. | |
| 2008/0161426 A1 | 7/2008 | Gudkov et al. | |
| 2008/0287382 A1 | 11/2008 | Feinstein et al. | |
| 2009/0082291 A1 | 3/2009 | Feinstein et al. | |
| 2009/0105173 A1 | 4/2009 | Feinstein | |
| 2010/0029746 A1 | 2/2010 | Feinstein | |
| 2010/0048425 A1 | 2/2010 | Khvorova et al. | |

FOREIGN PATENT DOCUMENTS

| | | |
|---|---|---|
| EP | 0430334 | 6/1991 |
| EP | 2284266 | 2/2011 |

(Continued)

OTHER PUBLICATIONS

Chiu et al., siRNA Function in RNAi: A Chemical modification analysis, RNA, (2003), 9:1034-1048.

(Continued)

*Primary Examiner* — Amy Bowman
(74) *Attorney, Agent, or Firm* — John P. White; Cooper & Dunham LLP

(57) ABSTRACT

The invention relates to one or more inhibitors, in particular siRNA compounds, which down-regulate the expression of a pro-apoptotic gene selected from the group consisting of TP53; HTRA2; KEAP1; SHC1-SHC, ZNHIT1, LGALS3 and HI95. The invention also relates to a pharmaceutical composition comprising the compound, and a pharmaceutically acceptable carrier. The present invention further provides methods of treating a subject afflicted with a disease or a condition associated with those genes, comprising administering to the subject a pharmaceutical composition in a therapeutically effective dose so as to thereby treat the subject.

20 Claims, No Drawings

(56) References Cited

FOREIGN PATENT DOCUMENTS

| | | |
|---|---|---|
| WO | WO 99/55910 | 11/1999 |
| WO | WO 00/24885 | 5/2000 |
| WO | WO 00/44895 | 8/2000 |
| WO | WO 00/44914 | 8/2000 |
| WO | WO 01/36646 | 5/2001 |
| WO | WO 01/68836 | 9/2001 |
| WO | WO 01/75164 | 10/2001 |
| WO | WO 02/44321 | 6/2002 |
| WO | WO 02/055693 | 7/2002 |
| WO | WO 02/059300 | 8/2002 |
| WO | WO 03/062394 | 7/2003 |
| WO | WO 03/064625 | 8/2003 |
| WO | WO 03/064626 | 8/2003 |
| WO | WO 03/070918 | 8/2003 |
| WO | WO 03/074654 | 9/2003 |
| WO | WO 2004/015107 | 2/2004 |
| WO | WO 2004/031237 | 4/2004 |
| WO | WO 2004/041889 | 5/2004 |
| WO | WO 2004/044136 | 5/2004 |
| WO | WO 2004/045543 | 6/2004 |
| WO | WO 2004/111191 | 12/2004 |
| WO | WO 2005/062937 | 7/2005 |
| WO | WO 2005/119251 | 12/2005 |
| WO | WO 2006/006948 | 1/2006 |
| WO | WO 2006/035434 | 4/2006 |
| WO | WO 2007/087451 | 8/2007 |
| WO | WO 2007/137129 | 11/2007 |
| WO | WO 2009/001359 | 12/2008 |
| WO | WO 2009/023025 | 2/2009 |
| WO | WO 2009/147684 | 12/2009 |

OTHER PUBLICATIONS

Hall et al., RNA interference using boranaphosphate siRNAs: structure-activity relationships, nucleic acids research, (2004), vol. 32(20):5991-6000.

Molitoris, BA (2003) "Transitioning to Therapy in Ischemic Acute Renal Failure." J. Am. Soc. Nephrol. 14: 265-267.

Scherer and Rossi (2004) Therapeutic Applications of RNA Interferences: Recent Advances in siRNA Design. Advances in Genetics 22:1-21.

Notice of Allowance and Allowed Claims in U.S. Appl. No. 12/586,271 (US 2010/0048425).

Oct. 26, 2009 Response to Second Written Opinion issued by the Australian Patent Office on May 26, 2009 in connection with Singapore Application No. 200702035-7.

Jan. 27, 2010 Exam Report and decision of grant in connection with Singapore Application No. 200702035-7.

Office Action issued by the Russian Patent Office on Jun. 2, 2010 in connection with Russian Patent Application No. 2007/116168.

Decision of Grant issued by the Russian Patent Office on Apr. 4, 2011 in connection with Russian Patent Application No. 2007/116168.

Notice of Allowance mailed on Jul. 22, 2010 in connection with Elena Feinstein et al., U.S. Appl. No. 11/827,199, filed Jul. 10, 2007.

First Office Action issued Mar. 29, 2010 in connection with Chinese Patent Application No. 200580032715.4 filed Sep. 27, 2005.

Aug. 12, 2010 Response and Amendment to First Office Action issued Mar. 29, 2010 in connection with Chinese Patent Application No. 200580032715.4 filed Sep. 27, 2005.

Amarzguioui et al., (2003), Nucleic Acids Research, 31(2):589-95, "Tolerance for Mutations and Chemical Modifications in a siRNA."

Barik, (2005) Mol. Med 2005, 83:764-773, "Silence of the transcripts; RNA Interference in Medicine".

Bartel et al., (2004), Cell, Jan. 23, 116(2):281-297, "MicroRNAs: Genomics, Review Biogenesis, Mechanism, and Function".

Bernstein et al., (2001), Nature, vol. 409:363-366, "Role for a Bidentate Ribonuclease in the Initiation Step of RNA Interference".

Bertrand et al (2002), "Comparison of antisense oligonucleotides and siRNAs in cell culture and in vivo", Biochemical and Biophysical Research Communications, 296:1000-1004.

Bitko et al., (2004), Nature Med., 11(1):50-55, "Inhibition of Respiratory Viruses by Nasally Administered siRNA".

Botchkarev et al., (2000), Cancer Research, 60:5002-5006 "p53 is Essential for Chemotherapy-Induced Hair Loss".

Brummelkamp et al., (2002), Science, vol. 296:550-553, "A System for Stable Expression of Short Interfering RNAs in Mammalian Cells".

Caplen et al., (2001), Proc Natl Acad Sci, 98(17):9742-9747, "Specific Inhibition of Gene Expression by Small Double-Stranded RNAs in Invertebrate Vertebrate Systems".

Chakraborty, (2007), Current Drug Targets, vol. 8(3):469-82, "Potentiality of Small Interfering RNAs (siRNA) as Recent Therapeutic Targets for Gene-Silencing".

Chalk et al., (2004), Biochem. Biophys. Res. Commun. Jun. 18; 319(1):264-274, "Improved and Automated Prediction of Effective siRNA."

Cheng, QL et al. (2000), "Effects of ICAM-1 antisense oligonucleotide on the tubulointerstitium in mice with unilateral ureteral obstruction", Kidney International, vol. 57:183-190.

Chernov et al., (1997), Oncogene 14:2503-2510, "The p53 Activation and Apoptosis Induced by DNA Damage are . . . ".

Cotsarelis et al., (2001), Trends Mol. Med. 7(7):293-301, "Towards a Molecular Understanding of Hair Loss and . . . ".

Czauderna et al., (2003), Nucleic Acids Research, 31(11):2705-16, "Structural Variations and Stabilising Modifications of Synthetic siRNAs in Mammalian Cells."

Dragon Duska et al. "Inhibition of intracellular adhesion molecule-1 with antisense deoxynucleotides prolongs renal isograft survival in the rat", Kidney International, Nature Publishing Group. vol. 54, No. 6, Dec. 1, 1998, pp. 2113-2122.

Elbashir et al., (2001), Genes Dev., 15 pp. 188-200, "RNA Interference is Mediated by 21- and 22-nucleotide RNAs".

Elbashir et al., (2001),Nature 411:494-498, "Duplexes of 21-nucleotide Mediated RNA Interference in Cultured Mammalian Cells".

Elbashir et al., (2001), Embo Journal, 20(23):6877-88, "Functional Anatomy of siRNAs for Mediating Efficient RNAi in *Drosophila melanogaster* Embryo Lysate."

Fire et al., (1998), Nature, vol. 391:806-811, "Potent and Specific Genetic Interference by Double-Stranded RNA in *Caenorhabditis elegans*."

Gottlieb TM et al., (1996) Biochim Biophys Acta 1287:77-102 "P53 in growth control and neoplasia."

Healy D et al. "Heat shock-induced protection of renal proximal tubular epithelial cells from cold storage and rewarming injury" Journal of the American Society of Nephrology. vol. 17, No. 3, Mar. 2006, pp. 805-812.

Hochegger Kathrin et al. "p21 and mTERT are novel markers for determining different ischemic time periods in renal ischemia-reperfusion injury", American Journal of Physiology. Renal Physiology Feb. 2007. pp. F762-F768.

Holen et al., (2002), Positional effects of short interfering RNAs targeting the human coagulation trigger Tissue Factor, Nucleic Acids Research, 30 (8) :1757-1766.

Kelly et al: "P53mediates the apoptotic response to GTP depletion after renal ischemia-reperfusion: Protective role of a p53 inhibitor", Journal of the American Society of Nephrology 2003 vol. 14, pp. 128-138.

Komarov PG et al., (1999) Science 285:1733-1737 "A chemical inhibitor of p53 that protects Mice from the Side Effects of Cancer Therapy".

Komarova EA et al., (1997) EMBO J. 16(6):1391-1400 "Transgenic mice with p53-responsive *lacZ*: p53 activity varies dramatically during normal development and determines radiation and drug sensitivity in vivo".

Lee et al., (2003), Nature, vol. 425:415-419, "The Nuclear RNase III Drosha Initiates mircoRNA Processing."

Levenkova et al., (2004), Bioinformatics 20(3):430-432, "Gene specific siRNA selector."

Mahato et al (2005) "Modulation of gene expression by antisense and antigene oligodeoxynucleotides and small interfering RNA", Expert Opinion on Drug Delivery, 2 (1):3-28.

Matta et al Cancer Biology & Therapy 2003, vol. 2, pp. 206- 210.

(56) References Cited

OTHER PUBLICATIONS

McManus et al., (2002), Nature Reviews Genetics, vol. 3:737-747, "Gene Silencing in Mammals by Small Interfering RNAs".
Molitoris, BA et al. (2009) "siRNA Targeted to P53 Attenuates Ischemic and Cisplatin-Induced Acute Kidney Injury". JASN Express, 20:1754:1764.
Perico Norberto et al. "Delayed graft function in kidney transplantation", Lancet (North American Edition), vol. 364, No. 9447, Nov. 13, 2004, pp. 1814-1827.
Prakash et al., (2005), "Positional effect of chemical modifications on short interference RNA activity in mammalian cells.", J. Med Chem. :48(13), pp. 4247-4253.
Scherer et al., (2003), Nat. Biotechnol., 21(12):1457-1465, "Approaches for the Sequence-Specific Knockdown of mRNA."
Schomber et al. (2004) Blood, (2004)103(12):4511-4513. "Gene silencing by lentivirus-mediated delivery of siRNA in human CD4+ cells."
Seidman M. et al., (2003). "Pharamcologic manipulation of the labyrinth with novel and traditional agents delivered to the inner ear", Ear, Nose & Throat Journal, 82(4):276-280, 282-283, 287-288, 290, 292, 294, 296, 298, 300.
Sioud et al., (2004), Methods in Molec Biol., 252:457-468, "Potential Design Rules and Enzymatic Synthesis of siRNAs".
Steele RJC et al., (1998) Br. J. Surg. 85:1460-1467 "The p53 tumour suppressor gene."
Supavekin, S. et al., (2003) "Differential gene expression following early renal ischemia/reperfusion". Kidney Int. 63:1714-1724.
Tekippe M et al., (2003) Exp. Hematol. 31:521-527 "Expansion of hematopoietic stem cell phenotype and activity in Trp53-null mice."
Tolentino et al., (2004), Journal of Retinal and Vitreous Diseases, Feb., 24(1):132-138, "Intravitreal Injection of Vascular Endothelial Growth Factor Small Interfering RNA Inhitits . . . ".
Ui-Tei et al., (2004), Nucleic Acids Research, vol. 32(3):936-48, "Guidelines for the Selection of Highly Effective siRNA Sequences for Mammalian and Chick RNA Interference . . . ".
Van De Water, Femke M. et al.(2006), "Intravenously administered short interfering RNA accumulates in the kidney and selectively suppresses gene function in renal proximal tubules", Drug Metabolism and Disposition vol. 34: 1393-1397.
Wang J et al. (2003). The J. of Neuroscience, 23(24):8596-8607. "A peptide inhibitor of c-Jun N-Terminal Kinase Protects against . . . ".
Wlodarski P et al., (1998) Blood 91(8):2998-3006 Role of p53 in hematopoietic recovery after cytotoxic treatment.
Zhang, M. et al., (2003). "Pifithrin-alpha Suppresses p53 and Protects Cochlear and Vestibular Hair Cells From Cisplatin-Induced Apoptosis," Neuroscience, 120:191-205.
Zhang et al., (2004) Current Pharmaceutical Biotechnology, 5:1-7,"Targeted Gene Silencing by Small RNA-Based Knock-Down Technology".
Office Action issued on Mar. 23, 2001 in connection with U.S. Appl. No. 09/493,527, filed Jan. 28, 2000.
Office Action issued on Jul. 2, 2001 in connection with U.S. Appl. No. 09/493,527, filed Jan. 28, 2000.
Office Action issued on Jun. 6, 2002 in connection with U.S. Appl. No. 09/493,527, filed Jan. 28, 2000.
Office Action issued on Feb. 12, 2003 in connection with U.S. Appl. No. 09/880,417, filed Jun. 13, 2001.
Office Action issued on Oct. 9, 2003 in connection with U.S. Appl. No. 09/880,417, filed Jun. 13, 2001.
Office Action issued on Jul. 9, 2004 in connection with U.S. Appl. No. 09/880,417, filed Jun. 13, 2001.
Office Action issued on Dec. 28, 2001 in connection with U.S. Appl. No. 09/947,757, filed Sep. 6, 2001.
Office Action issued on Mar. 26, 2003 in connection with U.S. Appl. No. 09/947,757, filed Sep. 6, 2001.
Office Action issued on Jul. 15, 2003 in connection with U.S. Appl. No. 09/947,757, filed Sep. 6, 2001.
Office Action issued on Nov. 19, 2003 in connection with U.S. Appl. No. 09/947,757, filed Sep. 6, 2001.
Office Action issued on Jul. 13, 2004 in connection with U.S. Appl. No. 09/947,757, filed Sep. 6, 2001.
Office Action issued on Nov. 26, 2004 in connection with U.S. Appl. No. 09/947,757, filed Sep. 6, 2001.
Office Action issued on Apr. 6, 2004 in connection with U.S. Appl. No. 10/350,560, filed Jan. 24, 2003.
Office Action issued on Jan. 3, 2005 in connection with U.S. Appl. No. 10/350,560, filed Jan. 24, 2003.
Office Action issued on Sep. 9, 2004 in connection with U.S. Appl. No. 10/352,597, filed Jan. 28, 2003.
Office Action issued on Apr. 21, 2005 in connection with U.S. Appl. No. 10/352,597, filed Jan. 28, 2003.
Office Action issued on Oct. 30, 2007 in connection with U.S. Appl. No. 11/136,231, filed May 24, 2005.
Office Action issued on Nov. 12, 2009 in connection with U.S. Appl. No. 12/022,317, filed Jan. 30, 2008.
International Search Report issued by the International Searching Authority (ISA/US) on Aug. 23, 2001 in connection with International Application No. PCT/US00/02104.
International Preliminary Examination Report by WIPO on May 15, 2001 in connection with International Application No. PCT/US00/02104.
Communication under Rule 112 EPC issued by the European Patent Office on Dec. 16, 2003 in connection with European Patent Application No. 00914455.1.
Communication pursuant to Article 96(2) EPC issued by the European Patent Office on Feb. 12, 2004 in connection with European Patent Application No. 00914455.1.
Communication pursuant to Article 96(2) EPC issued by the European Patent Office on Aug. 19, 2004 in connection with European Patent Application No. 00914455.1.
Communication pursuant to Article 96(2) EPC issued by the European Patent Office on May 13, 2005 in connection with European Patent Application No. 00914455.1.
Result of consultation issued by the European Patent Office on Oct. 25, 2005 in connection with European Patent Application No. 00914455.1.
Communication pursuant to Article 96(2) EPC issued by the European Patent Office on Mar. 10, 2006 in connection with European Patent Application No. 00914455.1.
Communication pursuant to Article 96(2) EPC issued by the European Patent Office on Oct. 24, 2006 in connection with European Patent Application No. 00914455.1.
Communication under Rule 51(4) EPC issued by the European Patent Office on Apr. 5, 2007 in connection with European Patent Application No. 00914455.1.
Notice of opposition issued on Sep. 11, 2008 in connection with European Patent Application No. 00914455.1.
Reply of the patent proprietor to the notice of opposition on Jun. 24, 2009, in connection with European Patent Application No. 00914455.1.
Written submission in preparation to oral proceedings issued on Oct. 8, 2010 in connection with European Patent Application No. 00914455.1.
Written submission in preparation to oral proceedings issued on Oct. 16, 2010 in connection with European Patent Application No. 00914455.1.
Written submission in preparation to oral proceedings issued on Nov. 30, 2010 in connection with European Patent No. 00914455.1.
Written submission in preparation to oral proceedings issued on Dec. 1, 2010 in connection with European Patent Application No. 00914455.1.
Decision of the Opposition Division issued by the European Patent Office on Feb. 10, 2011 in connection with European Patent Application No. 00914455.1.
Grounds for the decision (Annex)—opposition issued by the European Patent Office on Feb. 17, 2011 in connection with European Patent Application No. 00914455.1.
Office Action issued on Nov. 9, 2006 in connection with U.S. Appl. No. 11/237,598, filed Sep. 27, 2005.
Response to Office Action issued on Nov. 9, 2006 in connection with U.S. Appl. No. 11/237,598, filed Dec. 8, 2006.

(56) References Cited

OTHER PUBLICATIONS

Non-final Office Action issued on Mar. 14, 2007 in connection with U.S. Appl. No. 11/237,598, filed Sep. 27, 2005.
Response to Office Action issued on Mar. 14, 2007 in connection with U.S. Appl. No. 11/237,598, filed Sep. 14, 2007.
Final Office Action issued on Dec. 3, 2007 in connection with U.S. Appl. No. 11/237,598, filed Sep. 27, 2005.
Response to Final Office Action issued on Dec. 3, 2007 in connection with U.S. Appl. No. 11/237,598, filed May 5, 2008.
Advisory Action issued on Jun. 2, 2008 in connection with U.S. Appl. No. 11/237,598, filed Sep. 27, 2005.
Request for Continued Examination (RCE) filed on Jun. 3, 2008 in connection with U.S. Appl. No. 11/237,598, filed Sep. 27, 2005.
Supplemental Submission accompanying request for continued examination filed on Jul. 28, 2008.
Non-final Office Action issued on Oct. 28, 2008 in connection with U.S. Appl. No. 11/237,598, filed Sep. 27, 2005.
Response to Office Action issued Oct. 28, 2008 in connection with U.S. Appl. No. 11/237,598, filed Apr. 27, 2009.
Final Office Action issued on Aug. 19, 2009 in connection with U.S. Appl. No. 11/237,598, filed Sep. 27, 2005.
Notice of Appeal in connection with U.S. Appl. No. 11/237,598 filed Sep. 9, 2009.
Notice of Allowance mailed on Nov. 18, 2009 in connection with Elena Feinstein et al., U.S. Appl. No. 11/237,598, filed Sep. 27, 2005 and allowed claims.
Request for Continued Examination in connection with Elena Feinstein et al., U.S. Appl. No. 11/237,598, filed on Mar. 11, 2010.
Non-final Office Action issued on May 10, 2010, in connection with Elena Feinstein et al., U.S. Appl. No. 11/237,598, filed Sep. 27, 2005.
Response to Office Action issued on May 10, 2010 in connection with U.S. Appl. No. 11/237,598, filed Nov. 10, 2010.
Final Office Action issued on Feb. 15, 2011 in connection with U.S. Appl. No. 11/237,598, filed Sep. 27, 2005.
Pending claims in Elena Feinstein, et al., U.S. Appl. No. 11/237,598.
Non-Final Office Action issued on Sep. 23, 2009 in connection with U.S. Appl. No. 11/827,199, filed Jul. 10, 2007.
Response to Office Action issued on Sep. 23, 2009 in connection with U.S. Appl. No. 11/827, 199, filed Mar. 23, 2010.
Notice of Allowance mailed on Jul. 22, 2010 in connection with Elena Feinstein et al., U.S. Appl. No. 11/827,199, filed Jul. 10, 2007 and allowed claims.
Nov. 10, 2010 Issue Notification and issued claims in Elena Feinstein et al., U.S. Appl. No. 11/827,199, filed Jul. 10, 2007.
Pending claims in Elena Feinstein, et al., U.S. Appl. No. 12/008,578, filed Jan. 11, 2008.
Preliminary Amendment to the claims filed on Sep. 10, 2010 in connection with Elena Feinstein et al., U.S. Appl. No. 12/008,578, filed Jan. 11, 2008.
Non-final Official Action issued on Oct. 4, 2010, in connection with Elena Feinstein et al., U.S. Appl. No. 12/008,578, filed Jan. 11, 2008.
Response to Office Action issued on Oct. 4, 2010 in connection with U.S. Appl. No. 12/008,578, electronically filed on Dec. 3, 2010.
Supplemental Amendment submitted to supplement the Communication electronically filed on Dec. 3, 2010 in connection with U.S. Appl. No. 12/008,578, filed Dec. 28, 2010.
Non-final Official Action issued on Mar. 10, 2011, in connection with Elena Feinstein et al., U.S. Appl. No. 12/008,578, filed Jan. 11, 2008.
International Search Report issued by the International Searching Authority (ISA/US) on Dec. 3, 2007 in connection with International Application No. PCT/IL05/01035.
International Preliminary Report on Patentability issued by the International Searching Authority (ISA/US) on Apr. 2, 2009 in connection with International Application No. PCT/IL05/01035.
Written Opinion of the International Searching Authority (ISA/US) issued on Dec. 3, 2007 in connection with International Application No. PCT/IL05/01035.
Search Report issued by the Australian Patent Office on May 14, 2008 in connection with Singaporean Application/Patent No. 0702035-7.

Written Opinion issued by the Australian Patent Office on May 14, 2008 in connection with Singaporean Application/Patent No. 0702035-7.
Second Written Opinion issued by the Australian Patent Office on May 26, 2009 in connection with Singaporean Application No. 0702035-7.
Examination Report issued by the Australian Patent Office on Dec. 22, 2008 in connection with New Zealand Patent Application No. 553987.
Office Action issued by the Russian Patent Office on Jul. 20, 2009 in connection with Russian Patent Application No. 2007116168.
Office Action issued by the Japanese Patent Office on Feb. 8, 2011 in connection with Japanese Patent Application No. 2007-534174.
Non-final Office Action issued on May 1, 2008 in connection with U.S. Appl. No. 11/655,610, filed Jan. 18, 2007.
Response to Office Action issued on May 1, 2008 in connection with U.S. Appl. No. 11/655,610, filed Jun. 30, 2008.
Non-final Office Action issued on Oct. 2, 2008 in connection with U.S. Appl. No. 11/655,610, filed Jan. 18, 2007.
Response to Office Action issued on Oct. 2, 2008 in connection with U.S. Appl. No. 11/655,610, filed Dec. 31, 2008.
Notice of Allowance mailed on Apr. 7, 2009 in connection with Elena Feinstein et al., U.S. Appl. No. 11/655,610, filed Jan. 18, 2007 and allowed claims.
Amendment After Notice of Allowance filed on Sep. 22, 2010 in connection with Elena Feinstein, U.S. Appl. No. 11/655,610.
Oct. 13, 2010 Issue Notification and issued claims in Elena Feinstein, U.S. Appl. No. 11/655,610, filed Jan. 18, 2007.
Non-final Office Action issued on Jul. 22, 2009 in connection with U.S. Appl. No. 12/006,722, filed Jan. 4, 2008.
Response to Office Action issued on Jul. 22, 2009 in connection with U.S. Appl. No. 12/006,722, filed Jan. 21, 2010.
Non-final Office Action issued on Apr. 15, 2010 in connection with U.S. Appl. No. 12/006,722, filed Jan. 4, 2008.
Response to Office Action issued on Apr. 15, 2010 in connection with U.S. Appl. No. 12/006,722, filed Oct. 15, 2010.
Notice of Allowance mailed on Nov. 5, 2010 in connection with Elena Feinstein, U.S. Appl. No. 12/006,722, filed Jan. 4, 2008 and allowed claims.
Mar. 2, 2011 Issue Notification and issued claims in Elena Feinstein, U.S. Appl. No. 12/006,722, filed Jan. 4, 2008.
Non-final Official Action issued on Jan. 29, 2010, in connection with U.S. Appl. No. 12/459,617, filed Jul. 1, 2009.
Response to Office Action issued on Jan. 29, 2010 in connection with U.S. Appl. No. 12/459,617, filed Apr. 29, 2010.
Non-final Official Action issued on May 27, 2010, in connection with U.S. Appl. No. 12/459,617, filed Jul. 1, 2009.
Response to Office Action issued on May 27, 2010 in connection with U.S. Appl. No. 12/459,617, filed Nov. 24, 2010.
Final Official Action issued on Feb. 9, 2011, in connection with U.S. Appl. No. 12/459,617, filed Jul. 1, 2009.
Extended European Search Report issued May 17, 2011 in connection with European Patent Application No. 08763631.2.
International Search Report issued by the International Searching Authority (ISA/US) on Mar. 24, 2009 in connection with International Application No. PCT/EP2008/000874, filed Jun. 26, 2008.
International Search Report issued by the International Searching Authority (ISA/US) on Mar. 24, 2009 in connection with International Application No. PCT/IL2008/000874.
Written Opinion of the International Searching Authority (ISA/US) issued on Mar. 24, 2009 in connection with International Application No. PCT/IL2008/000874.
International Preliminary Report on Patentability issued by the International Searching Authority (ISA/US) on Jan. 19, 2010 in connection with International Application No. PCT/IL2008/000874.
Response and claim amendment filed Dec. 16, 2011 in reference to the Supplementary European Search Report dated May 17, 2011 in respect of EP 08763631.2 (EPO National Phase application of PCT/IL2008/000874).
Examination Report issued Jan. 20, 2012 in respect of EP 08763631.2 (EPO National Phase application of PCT/IL2008/000874).

(56) References Cited

OTHER PUBLICATIONS

Response to Examination Report issued Jan. 20, 2012 in respect of EP 08763631.2 (EPO National Phase application of PCT/IL2008/000874).

Claim amendments filed with the Response to Examination Report issued Jan. 20, 2012 in respect of EP 08763631.2 (EPO National Phase application of PCT/IL2008/000874).

Examination Report issued Nov. 26, 2012 in respect of EP 08763631.2 (EPO National Phase application of PCT/IL2008/000874).

COMPOSITIONS AND METHODS FOR REDUCING OR PROTECTING AGAINST DELAYED GRAFT FUNCTION (DGF)

This application is a §371 national stage application of PCT International Application No. PCT/IL2008/000874, filed Jun. 26, 2008, and claims the benefit of U.S. Provisional Applications Nos. 60/964,325, filed Aug. 10, 2007, and 60/937,318, filed Jun. 27, 2007, the contents of all of which are hereby incorporated by reference into this application.

This application incorporates-by-reference nucleotide and/or amino acid sequences which are present in the file named "184-PCT1 ST25 Apr. 2010.txt" which is 1,416,457 bytes in size, and which was created Apr. 21, 2010 in the IBM-PCT machine format, having an operating system compatibility with MS-Windows, which is contained on two duplicate compact discs labeled COPY 1 and COPY 2, and also labeled with the title, the name of each inventor, and the attorney docket number for this application.

Throughout this application various patent and scientific publications are cited. The disclosures for these publications in their entireties are hereby incorporated by reference into this application to more fully describe the state of the art to which this invention pertains.

FIELD OF THE INVENTION

The present invention relates to compounds, pharmaceutical compositions comprising same and methods of use thereof for the inhibition of certain pro-apoptotic genes, useful in the treatment of diseases and disorders in which gene expression is adverse. In particular embodiments, the invention provides siRNA oligonucleotides, compositions comprising same and methods of use thereof in the treatment of various diseases.

BACKGROUND OF THE INVENTION

RNA Interference

RNA interference (RNAi) is a phenomenon involving double-stranded (ds) RNA-dependent gene-specific posttranscriptional gene silencing. Originally, attempts to study this phenomenon and to manipulate mammalian cells experimentally were hindered by a non-specific antiviral defense mechanism activated in response to long dsRNA molecules (see Gil et al. Apoptosis 2000, 5:107-114). Later it was discovered that short, synthetic RNA duplexes of 21 nucleotides could mediate gene specific RNAi in mammalian cells, precluding stimulation of the generic antiviral defense mechanisms (see Elbashir et al. Nature 2001, 411:494-498; Caplen et al. PNAS USA 2001, 98:9742-9747). As a result, small interfering RNAs (siRNAs) have become powerful tools in attempting to understand gene function.

RNA interference (RNAi) in mammals is mediated by small interfering RNAs (siRNAs) (Fire et al, Nature 1998, 391:806) or microRNAs (miRNAs) (Ambros, Nature 2004, 431(7006):350-355; Bartel, Cell 2004, 116(2): 281-97). The corresponding process in plants is commonly referred to as specific post-transcriptional gene silencing (PTGS) or RNA silencing and is also referred to as quelling in fungi.

An siRNA is a double-stranded RNA or modified RNA molecule which down-regulates or silences (prevents) the expression of a gene/mRNA of its endogenous (cellular) counterpart. The mechanism of RNA interference is detailed infra.

Several studies have revealed that siRNA therapeutics is effective in vivo in both mammals and in humans. Bitko et al., have shown that specific siRNA molecules directed against the respiratory syncytial virus (RSV) nucleocapsid N gene are effective in treating mice when administered intranasally (Nat. Med. 2005, 11(1):50-55). Recent reviews discussing siRNA therapeutics are available (Barik, et al., J. Mol. Med. 2005, 83:764-773; Dallas and Vlassov, Med. Sci. Monitor 2006, 12(4):RA67-74; Chakraborty Current Drug Targets 2007, 8(3):469-82).

Mucke (IDrugs 2007 10(1):37-41) presents a review of current therapeutics, including siRNA to various targets, for the treatment of ocular diseases, for example age related macular degeneration (AMD) and glaucoma.

Pro-Apoptotic Genes

Pro-apoptotic genes are genes that encode proteins that play a role in apoptotic cell death. A non-limiting list of pro-apoptotic genes used in the present invention are: tumor protein p53 (P53 or TP53 which terms are used herein interchangeably); HtrA serine peptidase 2 (HTRA2); Kelch-like ECH associated protein 1 (KEAP1); Src homology 2 domain containing transforming protein 1 (SHC1-SHC, p66); zinc finger HIT type (ZNHIT1); lectin galactose-binding soluble 3 (LGALS3); and sestrin2 (HI95, SESN2).

Inhibition of one or more of the above genes is useful in the treatment and/or prevention of at least one of the following diseases or disorders and of other diseases disclosed herein: hearing loss, in particular chemical-induced ototoxicity, acute renal failure (ARF), chronic obstructive pulmonary disease (COPD), ischemia reperfusion injury following lung transplantation, lung cancer, acute respiratory disease syndrome (ARDS), spinal cord injury, pressure sores, osteoarthritis, diabetic retinopathy, oral mucositis, dry eye syndrome, ocular ischemic conditions and injury associated with organ transplant. The function of HI95 has been disclosed in Budanov et al., 2002, 21(39):6017-31.

Hearing Loss: Chemical-Induced Ototoxicity

The ototoxic effects of various therapeutic drugs on auditory cells and spiral ganglion neurons are often the limiting factor for their therapeutic usefulness. Main ototoxic drugs include the widely used chemotherapeutic agent cisplatin and its analogs, commonly used aminoglycoside antibiotics, e.g. gentamycin, for the treatment of infections caused by gram-negative bacteria, quinine and its analogs, salicylate and its analogs, and loop-diuretics.

For example, antibacterial aminoglycosides such as genta-mycins, streptomycins, kanamycins, tobramycins, and the like are known to have serious toxicity, particularly ototoxicity and nephrotoxicity, which reduce the value of such antimicrobials as therapeutic agents (see Goodman and Gilman's The Pharmacological Basis of Therapeutics, 6th ed., A. Goodman Gilman et al., eds; Macmillan Publishing Co., Inc., New York, 1980, pp. 1169-71).

Ototoxicity is a dose-limiting side-effect of antibiotic administration and of cisplatin, a platinum coordination complex, that has proven effective on a variety of human cancers including testicular, ovarian, bladder, and head and neck cancer. Platinum based drugs include carboplatin, cisplatin, oxaliplatin and satrapaltin inter alia; (see Kelland and Farrell eds., Platinum-based drugs in cancer therapy Human Press 2000; which is hereby incorporated by reference).

Cisplatin (Platinol®) and cisplatin-like compounds (platinum based compounds) damage auditory and vestibular systems.

Salicylates, such as aspirin, are the most commonly used therapeutic drugs for their anti-inflammatory, analgesic, antipyretic and anti-thrombotic effects. Unfortunately, they too have ototoxic side effects and can lead to tinnitus ("ringing in the ears") and temporary hearing loss. Moreover, if the drug is used at high doses for a prolonged time, chronic and irreversible hearing impairment can arise.

Without being bound by theory, it is believed that cisplatin drugs (cisplatin and cisplatin-like compounds) and other potentially ototoxic drugs (such as aminoglycoside antibiotics) may induce the ototoxic effects via programmed cell death or apoptosis in inner ear tissue, particularly inner ear hair cells (Mang et al., Neuroscience 2003, 120(1):191-205; Wang et al., J. Neuroscience 2003, 23(24):8596-8607). Presbycusis, age related hearing loss, is prevalent in the aging population with about 30-35 percent of adults between the ages of 65 and 75 years and about 40-50 percent of people aged 75 and older affected.

In mammals, auditory hair cells are produced only during embryonic development and do not regenerate if lost during postnatal life, therefore, loss of hair cells results in profound and irreversible deafness. Unfortunately, at present, there are no effective therapies to treat the cochlea and reverse this condition. Thus, an effective therapy to prevent cell death of auditory hair cells would be of great therapeutic value.

Accordingly, there exists a need for means to prevent, reduce or treat the incidence and/or severity diseases or disorders resulting from chemical toxicity including inner ear disorders and hearing impairment, renal damage (nephrotoxicity) and neural damage (neurotoxicity Acute Renal Failure Acute renal failure (ARF) is a clinical syndrome characterized by rapid deterioration of renal function that occurs within days. The principal feature of ARF is an abrupt decline in glomerular filtration rate (GFR), resulting in the retention of nitrogenous wastes (urea, creatinine). Worldwide, severe ARF occurs in about 170-200 per million population annually. To date, there is no specific treatment for established ARF. Several drugs have been found to ameliorate toxic and ischemic experimental ARF, as manifested by lower serum creatinine levels, reduced histological damage and faster recovery of renal function in different animal models. These include anti-oxidants, calcium channel blockers, diuretics, vasoactive substances, growth factors, anti-inflammatory agents and more. However, the drugs tested in clinical trials showed no benefit, and their use in clinical ARF has not been approved.

In the majority of hospitalized ARF patients, ARF is caused by acute tubular necrosis (ATN), which results from ischemic and/or nephrotoxic insults. Renal hypoperfusion is caused by hypovolemic, cardiogenic and septic shock, by administration of vasoconstrictive drugs, renovascular injury or kidney transplant. Nephrotoxins include exogenous toxins such as contrast media, aminoglycosides and cisplatin and cisplatin-like compounds as well as endogenous toxin such as myoglobin. Any chemical, biological or other agent which causes ARF or other kidney disease or disorder may be considered a nephrotoxin. Recent studies, however, support the theory that apoptosis in renal tissues is prominent in most human cases of ARF. The principal site of apoptotic cell death is the distal nephron. During the initial phase of ischemic injury, loss of integrity of the actin cytoskeleton leads to flattening of the epithelium, with loss of the brush border, loss of focal cell contacts, and subsequent disengagement of the cell from the underlying substratum. It has been suggested that apoptotic tubule cell death may be more predictive of functional changes than necrotic cell death (Komarov et al., Science 1999, 10; 285(5434):1733-7); Supavekin et al., Kidney Int. 2003, 63(5):1714-24).

In conclusion, currently there are no satisfactory modes of therapy for the prevention and/or treatment of acute renal failure, and there is a need therefore to develop novel compounds for this purpose.

Glaucoma

Glaucoma is one of the leading causes of blindness in the world. It affects approximately 66.8 million people worldwide and at least 12,000 Americans are blinded by this disease each year (Kahn and Milton, Am J. Epidemiol. 1980, 111(6):769-76). Glaucoma is characterized by the degeneration of axons in the optic nerve head, primarily due to elevated intraocular pressure (IOP). One of the most common forms of glaucoma, known as primary open-angle glaucoma (POAG), results from the increased resistance of aqueous humor outflow in the trabecular meshwork (TM), causing IOP elevation and eventual optic nerve damage.

Acute Respiratory Distress Syndrome

Acute respiratory distress syndrome (ARDS), also known as respiratory distress syndrome (RDS) or adult respiratory distress syndrome (in contrast with infant respiratory distress syndrome, IRDS) is a serious reaction to various forms of injuries to the lung. This is the most important disorder resulting in increased permeability pulmonary edema.

ARDS is a severe lung disease caused by a variety of direct and indirect insults. It is characterized by inflammation of the lung parenchyma leading to impaired gas exchange with concomitant systemic release of inflammatory mediators causing inflammation, hypoxemia and frequently resulting in multiple organ failure. This condition is life threatening, usually requiring mechanical ventilation and admission to an intensive care unit. A less severe form is called acute lung injury (ALI).

Spinal Cord Injury

Spinal cord injury or myelopathy, is a disturbance of the spinal cord that results in loss of sensation and/or mobility. The two common types of spinal cord injury are due to trauma and disease. Traumatic injury can be due to automobile accidents, falls, gunshot, diving accidents inter alia. and Diseases which can affect the spinal cord include polio, spina bifida, tumors and Friedreich's ataxia.

Ischemia Reperfusion Injury Following Lung Transplantation

Lung transplantation, the only definitive therapy for many patients with end stage lung disease, has poor survival rates in all solid allograft recipients. Ischemia reperfusion (IR) injury is one of the leading causes of death in lung allograft recipients.

Oral Mucositis

Oral mucositis, also referred to as a stomatitis, is a common and debilitating side effect of chemotherapy and radiotherapy regimens, which manifests itself as erythema and painful ulcerative lesions of the mouth and throat. Routine activities such as eating, drinking, swallowing, and talking may be difficult or impossible for subjects with severe oral mucositis. Palliative therapy includes administration of analgesics and topical rinses.

Dry Eye Syndrome

Dry eyes and dry eye syndrome are common problems usually resulting from a decrease in the production of tear film that lubricates the eyes. Most patients with dry eye experience discomfort, and no vision loss; although in severe cases, the cornea may become damaged or infected. Wetting drops (artificial tears) may be used for treatment while lubricating ointments may help more severe cases. Dry eyes is a hallmark symptom of Sjogren's syndrome.

Ocular Ischemic Conditions

Ischemic optic neuropathy (ION) includes a variety of disorders that produce ischemia to the optic nerve. By definition, ION is termed anterior if disc edema is present acutely, suggesting infarction of the portion of the optic nerve closest to the globe. ION also may be posterior, lying several centimeters behind the globe. Ischemic optic neuropathy usually occurs only in people older than 60 years of age. Most cases are nonarteritic and attributed to the effects of atherosclerosis, diabetes, or hypertension on optic nerve perfusion. Temporal arteritis causes about 5% of cases (arteritic ION).

Symptoms and signs are sudden, partial or complete vision loss, accompanied by swelling of the optic nerve head and often hemorrhage. Visual field defects may manifest as loss of half the visual field with a horizontal demarcation or as central or centrocecal (surrounding the natural blind spot) scotomata. Decreased vision is soon followed by pallor of the optic disk.

International patent application WO 00/44364 discloses TP53 inhibitors and their use for treatment of many diseases. International patent application no. WO 2006/035434 assigned to the assignee of the present invention discloses TP53 inhibitors for the treatment of, inter alia, acute renal failure and hearing loss). U.S. Pat. No. 7,074,895 assigned to the assignee of the present invention teaches full length HI95 polypeptide. GB 2420119 discloses certain KEAP1 siRNA. WO 03/087368 and WO 03/087367 teach methods of treating various eye and CNS diseases with RNAi to various target genes.

An effective therapy to treat the above mentioned diseases and disorders would be of great therapeutic value.

SUMMARY OF THE INVENTION

The present invention provides inhibitors of a pro-apoptotic gene selected from the group consisting of TP53; HTRA2; KEAP1; SHC1-SHC, ZNHIT1, LGALS3, and HI95. In particular the present invention provides novel double stranded oligonucleotides that inhibit or reduce expression of a pro-apoptotic gene selected from the group consisting of TP53; HTRA2; KEAP1; SHC1-SHC, ZNHIT1, LGALS3, and HI95, and pharmaceutical compositions comprising one or more such oligonucleotides or a vector capable of expressing the oligoribonucleotide. The present invention further relates to methods for treating or preventing the incidence or severity of various diseases or conditions in which gene expression is associated with the etiology or progression of the disease or condition.

In one aspect the present invention provides a compound having the structure:

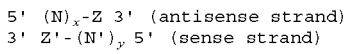

```
5'  (N)x-Z 3'  (antisense strand)
3'  Z'-(N')y 5'  (sense strand)
``` wherein each of N and N' is a nucleotide which may be modified or unmodified in its sugar residue;
wherein each of $(N)_x$ and $(N')_y$ is an oligonucleotide in which each consecutive N or N' is joined to the next N or N' by a covalent bond;
wherein each of x and y is an integer between 18 and 40;
wherein each of Z and Z' may be present or absent, but if present is 1-5 nucleotides covalently attached at the 3' terminus of the strand in which it is present; and
wherein the sequence of (N)x comprises an antisense sequence relative to the mRNA transcribed from a mammalian gene selected from the group consisting of TP53 (SEQ ID NO:3); HTRA2 (SEQ ID NOS:4-5); KEAP1 (SEQ ID NOS: 6-7); SHC1-SHC (SEQ ID NOS:8-9), ZNHIT1 (SEQ ID NO:10), LGALS3 (SEQ ED NOS:11-12), and HI95 (SEQ ID NO:13).

In some embodiments the compound comprises a phosphodiester bond. In various embodiments the compound comprises ribonucleotides wherein x=y and wherein x is an integer selected from the group consisting of 19, 20 and 21. In preferred embodiments x=y=19.

In some embodiments the compound is blunt ended, for example wherein Z and Z' are both absent. In an alternative embodiment, the compound comprises at least one 3' overhang, wherein at least one of Z or Z' is present. Z and Z' can be independently comprise one or more covalently linked modified or non-modified nucleotides, as described infra, for example inverted dT or dA; dT, LNA, mirror nucleotide and the like. In some embodiments each of Z and Z' are independently selected from dT and dTdT.

In some embodiments the compound comprises one or more ribonucleotides unmodified in their sugar residues. In other embodiments the compound comprises at least one ribonucleotide modified in the sugar residue. In some embodiments the compound comprises a modification at the 2' position of the sugar residue. Modifications in the 2' position of the sugar residue include amino, fluoro, methoxy, alkoxy and alkyl moieties. In certain preferred embodiments the modification comprises a ribonucleotide comprising a methoxy moiety at the 2' position (2'-O-methyl; 2'-O-Me; 2'-O—CH$_3$) of the sugar residue.

In some embodiments the compound comprises modified alternating ribonucleotides in one or both of the antisense and the sense strands. In preferred embodiments the compound comprises modified alternating ribonucleotides in the antisense and the sense strands. In some preferred embodiments the middle ribonucleotide of the antisense strand is not modified; e.g. ribonucleotide in position 10 in a 19-mer strand.

In additional embodiments the compound comprises modified ribonucleotides in alternating positions wherein the ribonucleotides at the 5' and 3' termini of the antisense strand are modified in their sugar residues, and the ribonucleotides at the 5' and 3' termini of the sense strand are unmodified in their sugar residues. In some embodiments, neither the antisense nor the sense strands are phosphorylated at the 3' and 5' termini. In other embodiments either or both the antisense and the sense strands are phosphorylated at the 3' termini.

In various embodiments the compound comprises an antisense sequence set forth in any one of SEQ ID NOS: 459-849, 1271-1691, 1873-2053, 2263-2471, 2697-2921, 3179-3435, 3578-3718, 3878-4035, 4198-4359, 4534-4709, 4870-5029, 5206-5381, 5726-6069, 6443-6815. In other embodiments the present invention provides a mammalian expression vector comprising an antisense sequence set forth in any one of SEQ ID NOS: 459-849, 1271-1691, 1873-2053, 2263-2471, 2697-2921, 3179-3435, 3578-3718, 3878-4035, 4198-4359, 4534-4709, 4870-5029, 5206-5381, 5726-6069, 6443-6815.

In certain preferred embodiments the present invention provides a compound having the structure

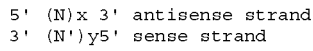

```
5'  (N)x 3'  antisense strand
3'  (N')y 5'  sense strand
``` wherein x and y=19; and (N)x and (N)y are fully complementary;
wherein alternating ribonucleotides in the antisense and the sense strands are modified to result in a 2'-O-methyl modification in the sugar residue of the ribonucleotides;

wherein the ribonucleotides at the 5' and 3' termini of the antisense strand are modified;
wherein the ribonucleotides at the 5' and 3' termini of the sense strand are unmodified;
wherein the antisense and the sense strands are phosphorylated or non-phosphorylated at the 3' and 5' termini; and
wherein each of Nx and N'y is selected from the group of oligomers set forth in SEQ ID NOS:68-6815. In certain embodiments the (N)x and (N')y are selected from the oligomers set forth in SEQ NOS:6816-7107.

In a second aspect the present invention provides a pharmaceutical composition comprising one or more compounds of the present invention, in an amount effective to inhibit human gene expression wherein the gene is selected from the group consisting of TP53; HTRA2; KEAP1; SHC1-SHC, ZNHIT1, LGALS3 and HI95; and a pharmaceutically acceptable carrier.

In another aspect, the present invention relates to a method for the treatment of a subject in need of treatment for a disease or disorder associated with the expression of a pro-apoptotic gene wherein the gene is selected from TP53; HTRA2; KEAP1; SHC1-SHC, ZNHIT1, LGALS3, and HI95, comprising administering to the subject an amount of an siRNA which reduces or inhibits expression of at least one of the pro-apoptotic genes.

More specifically, the present invention provides methods and compositions useful in treating a subject suffering from or at risk of acute renal failure (ARF), hearing loss including chemical-induced oxotoxicity, glaucoma, diabetic retinopathy, ischemic optic neuropathy (ION), dry eye syndrome, acute respiratory distress syndrome (ARDS) and other acute lung and respiratory injuries, injury (e.g. ischemia-reperfusion injury) in organ transplant including lung, kidney, bone marrow, heart, pancreas, cornea or liver transplantation, nephrotoxicity, nephritis, neurotoxicity, spinal cord injury, osteoarthritis (OA), oral mucositis, pressure sores, and chronic obstructive pulmonary disease (COPD).

The methods of the invention comprise administering to a subject in need thereof one or more inhibitory compounds which down-regulate expression of a pro-apoptotic gene selected from the group consisting of TP53; HTRA2; KEAP1; SHC1-SHC, ZNHIT1, LGALS3 and HI95; in a therapeutically effective dose so as to thereby treat the subject.

In various embodiments the inhibitor is selected from the group consisting of an siRNA, shRNA, an aptamer, an antisense molecule, miRNA, a ribozyme, and an antibody. In preferred embodiments the inhibitor is siRNA.

The present invention further relates to the use of compounds which down-regulate the expression of a proapoptotic gene, particularly to small interfering RNAs (siRNAs), in the treatment of various diseases, conditions or disorders associated with TP53; HTRA2; KEAP1; SHC1-SHC, ZNHIT1, LGALS3, and HI95 gene expression including acute renal failure (ARF), hearing loss including chemical-induced oxotoxicity, glaucoma, diabetic retinopathy, ischemic optic neuropathy, dry eye syndrome, acute respiratory distress syndrome (ARDS) and other acute lung and respiratory injuries, injury (e.g. ischemia-reperfusion injury) in organ transplant including lung, kidney, bone marrow, heart, pancreas, cornea or liver transplantation, nephrotoxicity, nephritis, neurotoxicity, spinal cord injury, osteoarthritis (OA), oral mucositis, pressure sores, and chronic obstructive pulmonary disease (COPD).

Another aspect of the invention provides a method of preventing or reducing the symptoms of Delayed Graft Function in a recipient of a kidney transplant, comprising administering to one or both of the donor and the recipient of the kidney transplant a composition comprising a therapeutically effective dose of a compound having the structure:

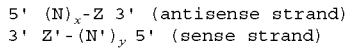

wherein each of N and N' is a nucleotide selected from an unmodified ribonucleotide, and a modified ribonucleotide;
wherein each of (N)x and (N')y is an oligomer in which each consecutive ribonucleotide is joined to the next ribonucleotide by a covalent bond and each of x and y is an integer between 18 and 40;
wherein in each of (N)x and (N')y the nucleotides alternate between modified ribonucleotides and unmodified ribonucleotides each modified ribonucleotide being modified so as to have a 2'-O-methyl on its sugar;
wherein each of Z and Z' may be present or absent, but if present is 1-5 deoxyribonucleotides covalently attached at the 3' terminus of the oligomer to which it is attached;
and wherein the antisense strand of the compound comprises the sequence UGAAGGGUGAAAUAUUCUC (SEQ ID NO:2) and the sense strand of the compound comprises the sequence GAGAAUAUUUCACCCUUCA (SEQ ID NO:1), thereby preventing or reducing the symptoms of Delayed Graft Function in the recipient.

Another aspect of the invention is a method of preventing or reducing the symptoms of Delayed Graft Function in a recipient of a kidney transplant, comprising administering to one or both of the donor and the recipient of the kidney transplant an oligonucleotide, preferably an siRNA, which reduces or inhibits expression of the TP53 gene, thereby preventing or reducing the symptoms of Delayed Graft Function in the recipient.

Lists of 19- and 21-mer sense and corresponding antisense sequences useful in preparation of siRNA compounds are set forth in SEQ ID NOS:68-6815.

A list of preferred siRNA to TP53 is provided in SEQ ID NOS:68-1691.

A list of preferred siRNA to HTRA2 is provided in SEQ ID NOS:1692-2471.

A list of preferred siRNA to KEAP1 is provided in SEQ ID NOS: 2472-3435.

A list of preferred siRNA to SHC1-SHC is provided in SEQ ID NOS:3436-4035.

A list of preferred siRNA to ZNHIT1 is provided in SEQ ID NOS:4036-4709.

A list of preferred siRNA to LGAL3 is provided in SEQ ID NOS:4710-5381.

A list of preferred siRNA to HI95 is provided in SEQ ID NOS:5382-6815.

Currently more preferred siRNA compounds are set forth in SEQ ID NOS:6816-s7107.

Known compounds, compositions and methods are explicitly excluded from the present invention.

These and further features of the present invention will be better understood in conjunction with the detailed description, examples and claims that follow.

DETAILED DESCRIPTION OF THE INVENTION

The present invention relates generally to compounds which down-regulate expression of TP53; HTRA2; KEAP1; SHC1-SHC, ZNHIT1, LGALS3, and HI95 genes, particularly to novel small interfering RNAs (siRNAs), and to the use of these siRNAs in the treatment of various diseases and medical conditions. Particular diseases and conditions to be treated are acute renal failure (ARF), hearing loss including chemical-induced oxotoxicity, glaucoma, diabetic retinopathy, ischemic optic neuropathy, dry eye syndrome, acute respiratory distress syndrome (ARDS) and other acute lung and respiratory injuries, injury (e.g. ischemia-reperfusion injury) in organ transplant including lung, kidney, bone marrow, heart, pancreas, cornea or liver transplantation, nephrotoxicity, nephritis, neurotoxicity, spinal cord injury, osteoarthritis (OA), oral mucositis, pressure sores, and chronic obstructive pulmonary disease (COPD).

Lists of preferred siRNA are provided in SEQ ID NOS:68-6815. The separate lists of 19-mer and 21-mer siRNAs are prioritized based on their score according to a proprietary algorithm as the best sequences for targeting the human gene expression. Methods, molecules and compositions, which inhibit the pro-apoptotic genes are discussed herein at length, and any of said molecules and/or compositions may be beneficially employed in the treatment of a subject suffering from or at risk of developing any of said conditions. 19-mer oligomers are set forth in SEQ ID NOS:68-849, 1692-2053, 2472-2921, 3436-3718, 4036-4359, 4710-5029 and 5382-6069. 21-mer oligomers are set forth in SEQ ID NOS:850-1691, 2054-2471, 2922-3435, 3720-4035, 4360-4709, 5030-5381 and 6070-6815. The oligomers are useful in the synthesis of siRNA compounds and pharmaceutical compositions comprising same.

DEFINITIONS

For convenience certain terms employed in the specification, examples and claims are described herein.

An "inhibitor" is a compound which is capable of inhibiting or reducing the expression or activity of a gene or the product of such gene to an extent sufficient to achieve a desired biological or physiological effect. The term "inhibitor" as used herein refers to one or more of an oligonucleotide inhibitor, including siRNA, shRNA, aptamers, antisense molecules, miRNA and ribozymes, as well as antibodies.

Table 1 below provides a list of the proapoptotic genes of the present invention, the gene identification (gi) numbers, as well as Genbank identifiers, known isoforms, and indications.

TABLE 1

| Gene | Full name and Human Gene ID | Indications or diseases to be treated according to the present invention* |
|---|---|---|
| p53 (TP53) | tumor protein p53 gi8400737, NM_000546.2 (SEQ ID NO: 3) | organ transplant (e.g. lung, kidney), glaucoma, hearing loss, acute kidney injury, acute lung injury, ischemic optic neuropathy (ION) |
| HTRA2 | Htra serine peptidase 2 var 1 gi: 73747817, NM_013247 (SEQ ID NO: 4) var 2 gi: 73747818, NM_145074 (SEQ ID NO: 5) | acute renal failure, hearing loss, ARDS, glaucoma, spinal cord injury, COPD, osteoarthritis, diabetic retinopathy, toxicity, organ transplant, acute ischemia-reperfusion lung injury |
| KEAP1 | Kelch-like ECH-associated protein 1 var 1 gi: 45269144 NM_203500 (SEQ ID NO: 6) var 2 gi: 45269143 NM_012289 (SEQ ID NO: 7) | acute renal failure, hearing loss, ARDS, glaucoma, spinal cord injury, COPD, osteoarthritis, diabetic retinopathy, pressure sores, nephrotoxicity, neurotoxicity, organ transplant |
| SHC1 | Src homology 2 domain containing) transforming prot. 1 var 1 gi: 52693920 NM_183001 (SEQ ID NO: 8) var 2 gi: 34147725 NM_003029 (SEQ ID NO: 9) | acute renal failure, hearing loss, ARDS, glaucoma, spinal cord injury, COPD, osteoarthritis, diabetic retinopathy, pressure sores, toxicity, organ transplant, acute ischemia-reperfusion lung injury |
| ZNHIT1 | Zn finger HIT type 1 gi: 37594439|; NM_006349 (SEQ ID NO: 10) | acute renal failure, hearing loss, ARDS, glaucoma, spinal cord injury, COPD, osteoarthritis, diabetic retinopathy, pressure sores, toxicity, organ transplant |
| LGALS3 | lectin galactoside-binding soluble 3 var 1 gi: 115430222 NM_002306 (SEQ ID NO: 11) var 2 gi: 115430224 NR_003225 (SEQ ID NO: 12) | acute renal failure, hearing loss, ARDS, glaucoma, spinal cord injury, COPD, osteoarthritis, diabetic retinopathy, pressure sores, organ transplant |
| HI95 | Sestrin2 gi: 32454742 NM_031459 (SEQ ID NO: 13) | acute renal failure, hearing loss, ARDS, glaucoma, spinal cord injury, COPD, osteoarthritis, diabetic retinopathy, pressure sores, organ transplant |

*Toxicity includes chemically induced (in a non-limiting example cisplatin and cisplatin analogs and aminoglycoside antibiotic ototoxicity, neurotoxicity and nephrotoxicity. Organ transplant includes inter alia lung, heart, kidney, liver and bone marrow.
ION: ischemic ocular neuropathy;
COPD: chronic obstructive pulmonary disorder;
ARDS: acute respiratory distress syndrome;

As used herein, the term "polypeptide" refers to, in addition to a polypeptide, an oligopeptide, peptide and a full protein. The present invention provides compounds that inhibit one or more isoforms of a gene, in the event that more than one isoforms exits.

RNA Interference and siRNA

RNA interference (RNAi) is based on the ability of dsRNA species to enter a cytoplasmic protein complex, where it is then targeted to the complementary cellular RNA and specifically degrade it. The RNA interference response features an endonuclease complex containing an siRNA, commonly referred to as an RNA-induced silencing complex (RISC), which mediates cleavage of single-stranded RNA having a sequence complementary to the antisense strand of the siRNA duplex. Cleavage of the target RNA may take place in the middle of the region complementary to the antisense strand of the siRNA duplex (Elbashir et al., Genes Dev., 2001, 15(2): 188-200). In more detail, longer dsRNAs are digested into short (17-29 bp) dsRNA fragments (also referred to as short inhibitory RNAs, "siRNAs") by type III RNAses (DICER, DROSHA, etc.; Bernstein et al., Nature, 2001, 409(6818): 363-6; Lee et al., Nature, 2003, 425(6956):415-9). The RISC protein complex recognizes these fragments and complementary mRNA. The whole process is culminated by endonuclease cleavage of target mRNA (McManus & Sharp, Nature Rev Genet, 2002, 3(10):737-47; Paddison & Hannon, Curr Opin Mol Ther. 2003, 5(3):217-24). (For additional information on these terms and proposed mechanisms, see for example Bernstein et al., RNA 2001, 7(11):1509-21; Nishikura, Cell 2001, 107(4):415-8 and PCT publication WO 01/36646).

The selection and synthesis of siRNA corresponding to known genes has been widely reported; see for example Ui-Tei et al., J Biomed Biotechnol. 2006; 2006: 65052; Chalk et al., Biochem. Biophys. Res. Comm. 2004, 319(1): 264-74; Sioud & Leirdal, Met. Mol. Biol.; 2004, 252:457-69; Levenkova et al., Bioinform. 2004, 20(3):430-2; Ui-Tei et al., Nuc. Acid Res. 2004, 32(3):936-48. For examples of the use of, and production of, modified siRNA see Braasch et al., Biochem., 2003, 42(26):7967-75; Chiu et al., RNA, 2003, 9(9): 1034-48; PCT publications WO 2004/015107 (Atugen); WO 02/44321 (Tuschl et al), and U.S. Pat. Nos. 5,898,031 and 6,107,094. See also Dykxhoorn et al Gene Therapy (2006), 13,541-552.

Several groups have described the development of DNA-based vectors capable of generating siRNA within cells. The method generally involves transcription of short hairpin RNAs that are efficiently processed to form siRNAs within cells (Paddison et al. PNAS USA 2002, 99:1443-1448; Paddison et al. Genes & Dev 2002, 16:948-958; Sui et al. PNAS USA 2002, 8:5515-5520; and Brummelkamp et al. Science 2002, 296:550-553). These reports describe methods to generate siRNAs capable of specifically targeting numerous endogenously and exogenously expressed genes.

As used herein, the term "nucleic acid" refers to polynucleotides such as deoxyribonucleic acid (DNA), and, where appropriate, ribonucleic acid (RNA). The terms should also be understood to include, as equivalents, analogs of either RNA or DNA made from nucleotide analogs, and, as applicable to the embodiment being described, double-stranded polynucleotides and single-stranded polynucleotides such as sense or antisense.

"Oligonucleotide" refers to a sequence having from about 2 to about 50 linked nucleotides or linked modified nucleotides, or a combination of modified and unmodified nucleotide. Oligonucleotide includes the terms oligomer, antisense strand and sense strand.

"Nucleotide" is meant to encompass deoxyribonucleotides and ribonucleotides, which may be natural or synthetic, and or modified or unmodified. Modifications include changes to the sugar moiety, the base moiety and or the linkages between ribonucleotides in the oligoribonucleotide.

All analogues of, or modifications to, a nucleotide/oligonucleotide may be employed with the present invention, provided that said analogue or modification does not substantially affect the function of the nucleotide/oligonucleotide. The nucleotides can be selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiouracil, 8-halo adenine, 8-aminoadenine, 8-thiol adenine, 8-thioalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other am and deaza adenines, other aza and deaza guanines, 5-trifluoromethyl uracil and 5-trifluoro cytosine.

In addition, analogues of polynucleotides can be prepared wherein the structure of one or more nucleotide is fundamentally altered and better suited as therapeutic or experimental reagents. An example of a nucleotide analogue is a peptide nucleic acid (PNA) wherein the deoxyribose (or ribose) phosphate backbone in DNA (or RNA) is replaced with a polyamide backbone which is similar to that found in peptides. PNA analogues have been shown to be resistant to enzymatic degradation and to have extended lives in vivo and in vitro. Other modifications that can be made to oligonucleotides include polymer backbones, cyclic backbones, acyclic backbones, thiophosphate-D-ribose backbones, triester backbones, thioate backbones, 2'-5' bridged backbone, artificial nucleic acids, morpholino nucleic acids, locked nucleic acid (LNA), glycol nucleic acid (GNA), threose nucleic acid (TNA), arabinoside, and mirror nucleoside (for example, beta-L-deoxynucleoside instead of beta-D-deoxynucleoside). Examples of siRNA compounds comprising LNA nucleotides are disclosed in Elmen et al., (NAR 2005. 33(1): 439-447).

The compounds of the present invention can be synthesized using one or more inverted nucleotides, for example inverted thymidine or inverted adenine (for example see Takei, et al., 2002. JBC 277(26):23800-06.

Certain structures include an siRNA compound having one or a plurality of 2'-5' internucleotide linkages (bridges).

A "mirror" nucleotide is a nucleotide with reversed chirality to the naturally occurring or commonly employed nucleotide, i.e., a mirror image (L-nucleotide) of the naturally occurring (D-nucleotide). The nucleotide can be a ribonucleotide or a deoxyribonucleotide and my further comprise at least one sugar, base and or backbone modification. U.S. Pat. No. 6,602,858 discloses nucleic acid catalysts comprising at least one L-nucleotide substitution.

The present invention provides methods and compositions for inhibiting expression of a pro-apoptotic gene in vivo. In general, the method includes administering oligoribonucleotides, in particular small interfering RNAs (i.e., siRNAs) or a nucleic acid material that can produce siRNA in a cell, that targets an mRNA transcribed from a pro-apoptotic gene in an amount sufficient to down-regulate expression of a target gene by an RNA interference mechanism. In particular, the subject method can be used to inhibit expression of pro-apoptotic gene for treatment of a disease.

In accordance with the present invention, the siRNA compounds or other inhibitors of the pro-apoptotic genes are used as drugs to treat various pathologies.

The present invention provides double-stranded oligoribonucleotides (eg. siRNAs), which down-regulate the expression of the pro-apoptotic genes selected from the group consisting of TP53; HTRA2; KEAP1; SHC1-SHC, ZNHIT1, LGALS3, and HI-95.

There are at least four variant TP53 polypeptides (Bourdon et al. *Genes Dev.* 2005; 19: 2122-2137). All variants are included in the definition of TP53 polypeptides and in the definition of the TP53 genes encoding them.

An siRNA of the invention is a duplex oligoribonucleotide in which the sense strand is derived from the mRNA sequence of the pro-apoptotic genes, and the antisense strand is complementary to the sense strand. In general, some deviation from the target mRNA sequence is tolerated without compromising the siRNA activity (see e.g. Czauderna et al., NAR 2003, 31(11):2705-2716). An siRNA of the invention inhibits gene expression on a post-transcriptional level with or without destroying the mRNA. Without being bound by theory, siRNA may target the mRNA for specific cleavage and degradation and/or may inhibit translation from the targeted message.

In some embodiments the oligoribonucleotide according to the present invention comprises modified siRNA. In various embodiments the siRNA comprises an RNA duplex comprising a first strand and a second strand, whereby the first strand comprises a ribonucleotide sequence at least partially complementary to about 18 to about 40 consecutive nucleotides of a target nucleic acid, and the second strand comprises ribonucleotide sequence at least partially complementary to the first strand and wherein said first strand and/or said second strand comprises a plurality of groups of modified ribonucleotides having a modification at the 2'-position of the sugar moiety whereby within each strand each group of modified ribonucleotides is flanked on one or both sides by a group of flanking ribonucleotides whereby each ribonucleotide forming the group of flanking ribonucleotides is selected from an unmodified ribonucleotide or a ribonucleotide having a modification different from the modification of the groups of modified ribonucleotides.

The group of modified ribonucleotides and/or the group of flanking ribonucleotides comprise a number of ribonucleotides selected from the group consisting of an integer from 1 to 10. Accordingly, the group thus comprises one nucleotide, two nucleotides, three nucleotides, four nucleotides, five nucleotides, six nucleotides, seven nucleotides, eight nucleotides, nine nucleotides or ten nucleotides.

The groups of modified nucleotides and flanking nucleotides may be organized in a pattern on at least one of the strands.

In some embodiments the first and second strands comprise a pattern of modified nucleotides. In various embodiments the pattern of modified nucleotides of said first strand is identical relative to the pattern of modified nucleotides of the second strand.

In other embodiments the pattern of modified nucleotides of said first strand is shifted by one or more nucleotides relative to the pattern of modified nucleotides of the second strand.

In some preferred embodiments the middle ribonucleotide in the first strand (antisense) is an unmodified nucleotide. For example, in a 19-oligomer antisense strand, ribonucleotide number 10 is unmodified; in a 21-oligomer antisense strand, ribonucleotide number 11 is unmodified; and in a 23-oligomer antisense strand, ribonucleotide number 12 is unmodified. The modifications or pattern of modification, if any, of the siRNA must be planned to allow for this.

The modifications on the 2' moiety of the sugar residue include amino, fluoro, alkoxy including methoxy, alkyl, amino, fluoro, chloro, bromo, CN, CF, imidazole, carboxylate, thioate, $C_1$ to $C_{10}$ lower alkyl, substituted lower alkyl, alkaryl or aralkyl, $OCF_3$, OCN, O—, S—, or N— alkyl; O—, S, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as described, inter alia, in European patents EP 0 586 520 B1 and EP 0 618 925 B1.

In some embodiments the siRNA is blunt ended, on one or both ends. More specifically, the siRNA may be blunt ended on the end defined by the 5'-terminus of the first strand and the 3'-terminus of the second strand, or the end defined by the 3'-terminus of the first strand and the 5'-terminus of the second strand, or both ends.

In other embodiments at least one of the two strands may have an overhang of at least one nucleotide at the 5'-terminus; the overhang may consist of at least one deoxyribonucleotide. At least one of the strands may also optionally have an overhang of at least one nucleotide at the 3'-terminus. The overhang may consist of from about 1 to about 4 nucleotides.

The length of RNA duplex is from about 18 to about 40 ribonucleotides, preferably 19 to 23 ribonucleotides. Further, the length of each strand (oligomer) may independently have a length selected from the group consisting of about 15 to about 40 bases, preferably 18 to 23 bases and more preferably 19, 20 or 21 ribonucleotides.

Additionally, in certain preferred embodiments the complementarity between said first strand and the target nucleic acid can be perfect. In some embodiments, the strands are substantially complementary, i.e. having one, two or up to three mismatches between said first strand and the target nucleic acid.

In some embodiments the first strand and the second strand each comprise at least one group of modified ribonucleotides and at least one group of flanking ribonucleotides, whereby each group of modified ribonucleotides comprises at least one ribonucleotide and whereby each group of flanking ribonucleotides comprises at least one ribonucleotide, wherein each group of modified ribonucleotides of the first strand is aligned with a group of flanking ribonucleotides on the second strand, and wherein the 5' most terminal ribonucleotide is selected from a group of modified ribonucleotides, and the 3' most terminal ribonucleotide of the second strand is a selected from the group of flanking ribonucleotide. In some embodiments each group of modified ribonucleotides consists of a single ribonucleotide and each group of flanking ribonucleotides consists of a single nucleotide.

In yet other embodiments the ribonucleotide forming the group of flanking ribonucleotides on the first strand is an unmodified ribonucleotide arranged in a 3' direction relative to the ribonucleotide forming the group of modified ribonucleotides, and the ribonucleotide forming the group of modified ribonucleotides on the second strand is a modified ribonucleotide which is arranged in 5' direction relative to the ribonucleotide forming the group of flanking ribonucleotides. In some embodiments the first strand of the siRNA comprises five to about twenty, eight to twelve, preferably ten or twelve groups of modified ribonucleotides, and the second strand comprises seven to eleven, preferably nine or eleven groups of modified ribonucleotides. The first strand and the second strand may be linked by a loop structure, which may be comprised of a non-nucleic acid polymer such as, inter alia, polyethylene glycol. Alternatively, the loop structure may be comprised of a nucleic acid, including modified and non-modified ribonucleotides and modified and non-modified deoxyribonucleotides.

Further, the 5'-terminus of the first strand of the siRNA may be linked to the 3'-terminus of the second strand, or the 3'-terminus of the first strand may be linked to the 5'-terminus of the second strand, said linkage being via a nucleic acid linker typically having a length between 3-100 nucleotides, preferably about 3 to about 10 nucleotides.

In various embodiments, the present invention provides a compound having structure A:

```
5' (N)x-Z 3'   (antisense strand)
3' Z'-(N')y 5' (sense strand)
``` wherein each N and N' is a ribonucleotide selected from the group consisting of a modified ribonucleotide or an unmodified ribonucleotide and each of $(N)_x$ and $(N')_y$ is an oligomer in which each consecutive N or N' is joined to the next N or N' by a covalent bond;

wherein each of x and y is an integer between 18 and 40;

wherein each of Z and Z' may be present or absent, but if present is 1-5 nucleotides covalently attached at the 3' terminus of the strand in which it is present;

and wherein the sequence of (N)x comprises an antisense sequence relative to the mRNA transcribed from a mammalian gene selected from the group consisting of TP53; HTRA2; KEAP1; SHC1-SHC, ZNHIT1, LGALS3, and HI95.

Z and Z' are preferably independently selected from the group consisting of dT (deoxythymine) and dTdT.

In certain embodiments the antisense and sense sequences are selected from the sequences set forth in SEQ ID NOS:68-6815. In preferred embodiments the antisense and sense 19mer sequences are selected from sequences set forth in SEQ ID NOS: 68-849, 1692-2053, 2472-2921, 3436-3718, 4036-4359, 4710-5029 and 5382-6069. All sequences are provided in 5'-3' orientation. Where cross-species specificity is known, the species is (are) listed, as well. The abbreviations in the tables are as follows: GIMP chimpanzee, MO mouse, CHL chinchilla, MK monkey, RB rabbit, GP guinea pig.

Certain preferred siRNA compounds comprise the following oligomer pairs (both sense and antisense oligomers are shown in 5'-3' orientation):

```
TP53: (#1 in Table A) (Sequence disclosed in
WO 2006/035434; I5)
Sense: GAGAAUAUUUCACCCUUCA
(SEQ ID NO: 2)
Antisense: UGAAGGGUGAAAUAUUCUC
(SEQ ID NO: 1)

TP53 (#44 in Table A) (Sequence disclosed in
WO 2006/035434; F3)
Sense: CCGAGUGGAAGGAAAUUUG
(SEQ ID NO: 7099)
Antisense: CAAAUUUCCUUCCACUCGG
(SEQ ID NO: 7102)

TP53 (#198 in Table A) (Sequence disclosed in
WO 2006/035434; G1)
Sense: GACAGAAACACUUUUCGAC
(SEQ ID NO: 7100)
Antisense: GUCGAAAAGUGUUUCUGUC
(SEQ ID NO: 7103)

HTRA2_11 (#2 in Table C and present in Table P)
Sense: GAAUCACAGAAACACUUUU
(SEQ ID NO: 6816)
Antisense: AAAAGUGUUUCUGUGAUUC
(SEQ ID NO: 6859)

HTRA2_ (#3 in Table C)
Sense: GGCCUGGUGAUGUGAUUUU
(SEQ ID NO: 1694)
Antisense: AAAAUCACAUCACCAGGCC
(SEQ ID NO: 1875)

HTRA2_13 (#5 in Table C)
Sense: CCGUGGUCUAUAUCGAGAU
(SEQ ID NO: 1696)
Antisense: AUCUCGAUAUAGACCACGG
(SEQ ID NO: 1877)

HTRA2_15 (#13 in Table C)
Sense: CCUAGCAACAUAUUAUAGU
(SEQ ID NO: 1704)
Antisense: ACUAUAAUAUGUUGCUAGG
(SEQ ID NO: 1885)

HTRA2_16 (#20 in Table C and present in Table P)
Sense: GCCGUGGUCUAUAUCGAGA
(SEQ ID NO: 1711)
Antisense: UCUCGAUAUAGACCACGGC
(SEQ ID NO: 1892)

HTRA2_17 (#55 in Table C and present in Table P)
Sense: GUGCUGCUCUUUGUGGUGU
(SEQ ID NO: 1746)
Antisense: ACACCACAAAGAGCAGCAC
(SEQ ID NO: 1927)

HTRA2_18 (#179 in Table C)
Sense: CAGCUAUUGAUUUUGGAAA
(SEQ ID NO: 1870)
Antisense: UUUCCAAAAUCAAUAGCUG
(SEQ ID NO: 2051)

HTRA2_21 (#180 in Table C)
Sense: GCUAUUGAUUUUGGAAACU
(SEQ ID NO: 1871)
Antisense: AGUUUCCAAAAUCAAUAGC
(SEQ ID NO: 2052)

HTRA2_22 (#181 in Table C)
Sense: AGCUAUUGAUUUUGGAAAC
(SEQ ID NO: 1872)
Antisense: GUUUCCAAAAUCAAUAGCU
(SEQ ID NO: 2053)

KEAP1_2 (#5 in Table E)
Sense: GCCUCAUUGAAUUCGCCUA
(SEQ ID NO: 2476)
Antisense: UAGGCGAAUUCAAUGAGGC
(SEQ ID NO: 2701)

KEAP1_11 (#20 in Table E and present in Table P)
Sense: CACCAUGUGAUUUAUUCUU
(SEQ ID NO: 2491)
Antisense: AAGAAUAAAUCACAUGGUG
(SEQ ID NO: 2716)

KEAP1_12 (#21 in Table E and present in Table P)
Sense: ACUGCAAAUAACCCAUCUU
(SEQ ID NO: 2492)
Antisense: AAGAUGGGUUAUUUGCAGU
(SEQ ID NO: 2717)

KEAP1_13 (#28 in Table E and present in Table P)
Sense: CACUGCAAAUAACCCAUCU
(SEQ ID NO: 2499)
Antisense: AGAUGGGUUAUUUGCAGUG
(SEQ ID NO: 2724)

KEAP1_14 (#37 in Table E and present in Table P)
Sense: GCAGCUGUCACCAUGUGAU
(SEQ ID NO: 2508)
Antisense: AUCACAUGGUGACAGCUGC
(SEQ ID NO: 2733)

KEAP1_17 (#56 in Table E and present in Table P)
Sense: UGCAUCAACUGGGUCAAGU
(SEQ ID NO: 2527)
Antisense: ACUUGACCCAGUUGAUGCA
(SEQ ID NO: 2752)
```

```
SHC1_1 (#1 in Table G)
Sense: ACCUGAAAUUUGCUGGAAU
(SEQ ID NO: 3436)
Antisense: AUUCCAGCAAAUUUCAGGU
(SEQ ID NO: 3578)

SHC1_2 (#3 in Table G)
Sense: CAGAGAGCUUUUUGAUGAU
(SEQ ID NO: 3438)
Antisense: AUCAUCAAAAAGCUCUCUG
(SEQ ID NO: 3580)

SHC1_3 (#8 in Table G)
Sense: CACAUGCAAUCUAUCUCAU
(SEQ ID NO: 3443)
Antisense: AUGAGAUAGAUUGCAUGUG
(SEQ ID NO: 3585)

SHC1_6 (#28 in Table G)
Sense: CGGGAGCUUUGUCAAUAAG
(SEQ ID NO: 3463)
Antisense: CUUAUUGACAAAGCUCCCG
(SEQ ID NO: 3605)

SHC1_8 (#140 in Table G)
Sense: GGGUUCUUAUAAUGGAAAA
(SEQ ID NO: 3575)
Antisense: UUUUCCAUUAUAAGAACCC
(SEQ ID NO: 3717)

SHC1_11 (#141 in Table G)
Sense: CCCAAGCCCAAGUACAAUC
(SEQ ID NO: 3576)
Antisense: GAUUGUACUUGGGCUUGGG
(SEQ ID NO: 3718)

SHC1_14 (#142 in Table G)
Sense: AGGAAGGGCAGCUGAUGAU
(SEQ ID NO: 3577)
Antisense: AUCAUCAGCUGCCCUUCCU
(SEQ ID NO: 3719)

ZNHIT1_1 (#1 in Table I)
Sense: CCGAGGUGAUCAUUUUAAA
(SEQ ID NO: 4036)
Antisense: UUUAAAAUGAUCACCUCGG
(SEQ ID NO: 4198)

ZNHIT1_5 (#5 in Table I)
Sense: GUGACCACAUCUUUAAAAU
(SEQ ID NO: 4040)
Antisense: AUUUUAAAGAUGUGGUCAC
(SEQ ID NO: 4202)

ZNHIT1_10 (#34 in Table I)
Sense: CUGGAAAGAAAAAGAAGAA
(SEQ ID NO: 4069)
Antisense: UUCUUCUUUUUCUUUCCAG
(SEQ ID NO: 4231)

ZNHIT1_11 (#50 in Table I)
Sense: ACACUGGAAAGAAAAAGAA
(SEQ ID NO: 4085)
Antisense: UUCUUUUUCUUUCCAGUGU
(SEQ ID NO: 4247)

LGALS3_3: (#4 in Table K)
Sense: GGGAAUUUCUGGUGACAUA
(SEQ ID NO: 4713)
Antisense: UAUGUCACCAGAAAUUCCC
(SEQ ID NO: 4873)

LGALS3_5: (#159 in Table K)
Sense: GCAGACGGCUUCUCACUUA
(SEQ ID NO: 4868)
Antisense: UAAGUGAGAAGCCGUCUGC
(SEQ ID NO: 5028)

LGALS3_17 (#160 in Table K and present in Table P)
Sense: AGCGGAAAAUGGCAGACAA
(SEQ ID NO: 4869)
Antisense: UUGUCUGCCAUUUUCCGCU
(SEQ ID NO: 5029)

LGALS3_18 (#15 in Table K)
Sense: GGGUUAAAAAACUCAAUGA
(SEQ ID NO: 4724)
Antisense: UCAUUGAGUUUUUUAACCC
(SEQ ID NO: 4884)
```

It will be readily understood by those skilled in the art that the compounds of the present invention consist of a plurality of modified and/or unmodified ribonucleotides, which are linked through covalent linkages. Each such covalent linkage may be a phosphodiester linkage, a phosphorothioate linkage, or a combination of both, along the length of the ribonucleotide sequence of the individual strand. Other possible backbone modifications are described inter alia in U.S. Pat. Nos. 5,587,361; 6,242,589; 6,277,967; 6,326,358; 5,399,676; 5,489,677; 5,596,086; 6,693,187 and 7,067,641.

In particular embodiments, x and y are independently an integer between about 18 to about 40, preferably from about 19 to about 23. In a particular embodiment, x is equal to y (i.e. x=y) and in preferred embodiments x=y=19, x=y=20 or x=y=21. In a particularly preferred embodiment x=y=19.

In one embodiment of the compound of the invention, Z and Z' are both absent; in another embodiment one or both of Z or Z' is present.

In one embodiment all of the ribonucleotides of the compound are unmodified in their sugar residues.

In certain preferred embodiments at least one ribonucleotide is modified in its sugar residue, preferably by the addition of a moiety at the 2' position. A preferred moiety is selected from the group consisting of amino, fluoro, alkoxy and alkyl groups. In certain embodiments the alkozy moiety is methoxy. In a presently preferred embodiment the moiety at the 2' position is methoxy (2'-O-Me).

In preferred embodiments of the invention, alternating ribonucleotides are modified in both the antisense and the sense strands of the compound. In particular the exemplified siRNA has been modified such that a 2'-O-methyl (Me) group was present on the first, third, fifth, seventh, ninth, eleventh, thirteenth, fifteenth, seventeenth and nineteenth nucleotide of the antisense strand, whereby the very same modification, i.e. a 2'-O-Me group, was present at the second, fourth, sixth, eighth, tenth, twelfth, fourteenth, sixteenth and eighteenth nucleotide of the sense strand. Additionally, it is to be noted that these particular siRNA compounds are also blunt ended.

In various preferred embodiments the compounds of the invention comprise alternating modified and unmodified ribonucleotides in both the antisense and the sense strands of the compound. In certain embodiments in the 19-mer oligomers and 23-mer oligomers the ribonucleotides at the 5' and 3' termini of the antisense strand are modified in their sugar residues, and the ribonucleotides at the 5' and 3' termini of the sense strand are unmodified in their sugar residues. For 21-mer oligomers the ribonucleotides at the 5' and 3' termini of the sense strand are modified in their sugar residues, and the ribonucleotides at the 5' and 3' termini of the antisense strand are unmodified in their sugar residues. As mentioned above, it is preferred that the middle nucleotide of the antisense strand is unmodified.

According to one preferred embodiment of the invention, the antisense and the sense strands of the siRNA are phosphorylated only at the 3'-terminus and not at the 5'-terminus. According to another preferred embodiment of the invention, the antisense and the sense strands are non-phosphorylated. According to yet another preferred embodiment of the invention, the 5' ribonucleotide in the sense strand is modified, for example to abolish any possibility of in vivo 5'-phosphorylation.

The invention further provides a vector capable of expressing any of the aforementioned oligoribonucleotides in unmodified form in a cell after which appropriate modification may be made. In preferred embodiment the cell is a mammalian cell, preferably a human cell.

Substantially complementary refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary.

Accordingly substantially identical refers to identity of greater than about 84%, to another sequence.

More particularly, the invention provides an oligoribonucleotide wherein one strand comprises consecutive nucleotides having, from 5' to 3', the sequence set forth in SEQ ID NOS:68-6815 or a homolog thereof wherein in up to two of the ribonucleotides in each terminal region is altered.

The terminal region of the oligoribonucleotide refers to bases 1-4 and/or 16-19 in the 19-mer oligomer sequence and to bases 1-4 and/or 18-21 in the 21-mer oligomer sequence.

SEQ ID NOS:68-6815 provide 19- and 21-mer oligomers useful in the preparation of siRNA compounds for targeting the expression of a gene selected from TP53; HTRA2; KEAP1; SHC1—SHC, ZNHIT1, LGALS3, and HI95 respectively. The presently most preferred compound of the invention is a blunt-ended 19-mer siRNA, i.e. x=y=19 and Z and Z' are both absent. The siRNA is either phosphorylated at 3' termini of both sense and anti-sense strands, or non-phosphorylated at all; or having the 5' most ribonucleotide on the sense strand specifically modified to abolish any possibility of in vivo 5'-phosphorylation. The alternating ribonucleotides are modified at the 2' position of the sugar residue in both the antisense and the sense strands, wherein the moiety at the 2' position is methoxy (2'-O-methyl) and wherein the ribonucleotides at the 5' and 3' termini of the antisense strand are modified in their sugar residues, and the ribonucleotides at their 5' and 3' termini of the sense strand are unmodified in their sugar residues.

The compounds of the present invention can be synthesized by any of the methods that are well known in the art for synthesis of ribonucleic (or deoxyribonucleic) oligonucleotides. Such synthesis is, among others, described in Beaucage and Iyer Tetrahedron 1992; 48: 2223-2311, Beaucage and Iyer, Tetrahedron 1993; 49: 6123-6194 and Caruthers et. al., Methods Enzymol. 1987; 154: 287-313; the synthesis of thioates is, among others, described in Eckstein, Arum. Rev. Biochem. 1985; 54: 367-402, the synthesis of RNA molecules is described in Sproat, in Humana Press 2005, Herdewijn ed.; Kap. 2: 17-31 and respective downstream processes are, among others, described in Pingoud et al., in IRL Press 1989 edited by Oliver; Kap. 7: 183-208 and Sproat (ibid).

Other synthetic procedures are known in the art e.g. the procedures as described in Usman et al., 1987, J. Am. Chem. Soc., 109, 7845; Scaringe et al., 1990, NAR, 18, 5433; Wincott et al., 1995, NAR, 23, 2677-2684; and Wincott et al., 1997, Methods Mol. Bio., 74, 59, and these procedures may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

The oligonucleotides of the present invention can be synthesized separately and joined together post-synthetically, for example, by ligation (Moore et al., 1992, Science 256, 9923; International PCT publication No, WO 93/23569; Shabarova et al., 1991, NAR 19, 4247; Bellon et al., 1997, Nucleosides & Nucleotides, 16, 951; Bellon et al., 1997, Bioconj. Chem. 8, 204), or by hybridization following synthesis and/or deprotection.

It is noted that a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the siRNAs or siRNA fragments of the present invention, two or more such sequences can be synthesized and linked together for use in the present invention.

The compounds of the invention can also be synthesized via a tandem synthesis methodology, as described in US patent application publication No. 2004/0019001 wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker can be a polynucleotide linker or a non-nucleotide linker.

Pharmaceutical Compositions

While it may be possible for the compounds of the present invention to be administered as the raw chemical, it is preferable to present them as a pharmaceutical composition. Accordingly the present invention provides a pharmaceutical composition comprising one or more of the compounds of the invention; and a pharmaceutically acceptable carrier. This composition may comprise a mixture of two or more different siRNA compounds.

The invention further provides a pharmaceutical composition comprising at least one compound of the invention covalently or non-covalently bound to one or more compounds of the invention in an amount effective to inhibit the mammalian pro-apoptotic genes; and a pharmaceutically acceptable carrier. The compound may be processed intracellularly by endogenous cellular complexes to produce one or more oligoribonucleotides of the invention.

The invention further provides a pharmaceutical composition comprising a pharmaceutically acceptable carrier and one or more of the compounds of the invention in an amount effective to down-regulate expression in a cell of a mammalian pro-apoptotic gene of the present invention, the compound comprising a sequence substantially complementary to the sequence of $(N)_x$ Methods of Treatment In preferred embodiments the subject being treated is a warm-blooded animal and, in particular, mammals including human, afflicted with or suffering from a disease or disorder associated with TP53; HTRA2; KEAP1; SHC1-SHC, ZNHIT1, LGALS3, and HI95 expression.

The term "treatment" as used herein refers to administration of a therapeutic substance to a subject in need thereof in an amount effective to ameliorate symptoms associated with a disease, to lessen the severity or cure the disease, or to prevent the disease from occurring.

In cases where treatment is for the purpose of prevention, then the present invention relates to a method for delaying the onset of or averting the development of the disease or disorder.

The term "organ transplant" is meant to encompass transplant of any one or more of the following organs including, inter alia, lung, kidney, bone marrow, heart, pancreas, cornea, skin, vein, bone, cartilage, liver transplantation. Although a xenotransplant can be contemplated in certain situations, an allotransplant is usually preferable. An autograft can be considered for bone marrow, skin, bone, cartilage and or blood vessel transplantation.

For organ transplantation, either the donor or the recipient or both may be treated with a compound or composition of the present invention. Accordingly, the present invention relates to a method of treating an organ donor or an organ recipient comprising the step of administering to the organ donor or organ recipient a therapeutically effective amount of a compound according to the present invention.

The invention further relates to a method for preserving an organ comprising contacting the organ with an effective amount of compound of the present invention. Also provided is a method for reducing or preventing injury (in particular reperfusion injury) of an organ during surgery and/or following removal of the organ from a subject comprising placing the organ in an organ preserving solution wherein the solution comprises a compound according to the present invention.

Additionally, the invention provides a method of down-regulating the expression of a mammalian pro-apoptotic genes selected from the group consisting of TP53; HTRA2; KEAP1; SHC1-SHC, LGALS3, and HI95 by at least 50% as compared to a control comprising contacting a mRNA transcript selected from the group consisting of TP53 (SEQ ID NO:3); HTRA2 (SEQ ID NOS:4-5); KEAP1 (SEQ ID NOS:6-7); SHC1-SHC (SEQ ID NOS:8-9), ZNHIT1 (SEQ ID NO:10), LGALS3 (SEQ ID NOS:11-12), and HI95 (SEQ ID NO:13).; respectively with one or more of the compounds of the present invention.

In one embodiment the compound of the present invention down-regulates one of the mammalian genes selected from the group consisting of TP53; HTRA2; KEAP1; SHC1-SHC, ZNHIT1, LGALS3, and HI95 whereby the down-regulation is selected from the group comprising down-regulation of gene function, down-regulation of polypeptide and down-regulation of mRNA expression.

In one embodiment the compound is down-regulating a mammalian pro-apoptotic polypeptide, whereby the down-regulation is selected from the group comprising down-regulation of function (which may be examined by an enzymatic assay or a binding assay with a known interactor of the native gene/polypeptide, inter alia), down-regulation of protein (which may be examined by Western blotting, ELISA or immuno-precipitation, inter alia) and down-regulation of mRNA expression (which may be examined by Northern blotting, quantitative RT-PCR, in-situ hybridization or microarray hybridization, inter alia).

In additional embodiments the invention provides a method of treating a patient suffering from a disease accompanied by an elevated level of a mammalian pro-apoptotic gene disclosed herein, the method comprising administering to the patient a compound or composition of the invention in a therapeutically effective dose thereby treating the patient.

The present invention relates to the use of compounds which down-regulate the expression of a mammalian pro-apoptotic gene, particularly to novel small interfering RNAs (siRNAs), in the treatment of the following diseases or conditions in which inhibition of the expression of the mammalian TP53; HTRA2; KEAP1; SHC1-SHC, ZNHIT1, LGALS3, and HI95 genes is beneficial: acute renal failure (ARF), hearing loss including chemical-induced oxotoxicity, glaucoma, diabetic retinopathy, ischemic optic neuropathy, dry eye syndrome, acute respiratory distress syndrome (ARDS) and other acute lung and respiratory injuries, injury (e.g. ischemia-reperfusion injury) in organ transplant including lung, kidney, bone marrow, heart, pancreas, cornea or liver transplantation, nephrotoxicity, nephritis, neurotoxicity, spinal cord injury, osteoarthritis (OA), oral mucositis, pressure sores, and chronic obstructive pulmonary disease (COPD).

Other indications include chemical-induced nephrotoxicity and chemical-induced neurotoxicity, for example toxicity induced by cisplatin and cisplatin-like compounds (platinum-based compounds), by aminoglycosides, by loop diuretics, and by hydroquinone and their analogs.

Methods, molecules and compositions which inhibit a mammalian proapoptotic gene or polypeptide of the present invention are discussed herein at length, and any of said molecules and/or compositions may be beneficially employed in the treatment of a patient suffering from any of said conditions. It is to be explicitly understood that the present invention covers novel compounds and compositions as well as novel methods of treatment of known compounds (such as the compounds disclosed in co-assigned PCT Publication No. WO 2006/035434.

"Treatment" refers to both therapeutic treatment and prophylactic or preventative measures, wherein the object is to prevent or slow down (lessen) pro-apoptotic-related disorder as listed above. Those in need of treatment include those already experiencing the disease or condition, those prone to having the disease or condition, and those in which the disease or condition is to be prevented. The compounds of the invention may be administered before, during or subsequent to the onset of the disease or condition.

The method of the invention includes administering a therapeutically effective amount of one or more compounds which down-regulate expression of TP53; HTRA2; KEAP1; SHC1-SHC, ZNHIT1, LGALS3, and HI95 genes, particularly the novel siRNAs of the present invention, small molecule inhibitors of the a pro-apoptotic gene or protein or antibodies to the a pro-apoptotic proteins.

In some preferred embodiments, the methods of the invention are applied to various conditions of hearing loss. Without being bound by theory, the hearing loss may be due to inner ear hair cell damage or loss, wherein the damage or loss is caused by, inter alia, infection, mechanical injury, loud sound, aging (presbycusis or loss of hearing that gradually occurs in most individuals as they grow older), or chemical-induced ototoxicity. Ototoxins include therapeutic drugs including antineoplastic agents, salicylates, quinines, and aminoglycoside antibiotics, contaminants in foods or medicinals, and environmental or industrial pollutants. Typically, treatment is performed to prevent or reduce ototoxicity, especially resulting from or expected to result from administration of therapeutic drugs. Preferably a therapeutically effective composition is given immediately after the exposure to prevent or reduce the ototoxic effect. More preferably, treatment is provided prophylactically, either by administration of the composition prior to or concomitantly with the ototoxic pharmaceutical or the exposure to the ototoxin.

By "ototoxin" in the context of the present invention is meant a substance that through its chemical action injures, impairs or inhibits the activity of the sound receptors component of the nervous system related to hearing, which in turn impairs hearing (and/or balance). In the context of the present invention, ototoxicity includes a deleterious effect on the inner ear hair cells. Ototoxic agents that cause hearing impairments include, but are not limited to, neoplastic agents such as vincristine, vinblastine, cisplatin and cisplatin-like compounds, taxol and taxol-like compounds, dideoxy-compounds, e.g., dideoxyinosine; alcohol; metals; industrial toxins involved in occupational or environmental exposure; contaminants of food or medicinals; and over-doses of vitamins or therapeutic drugs, e.g., antibiotics such as penicillin or chloramphenicol, and megadoses of vitamins A, D, or B6, salicylates, quinines and loop diuretics.

The ototoxic effects of various therapeutic drugs on auditory cells and spiral ganglion neurons are often the limiting factor for their therapeutic usefulness. Main ototoxic drugs include the widely used chemotherapeutic agent cisplatin and its analogs, commonly used aminoglycoside antibiotics, e.g. gentamicin, for the treatment of infections caused by gram-negative bacteria, quinine and its analogs, salicylate and its analogs, and loop-diuretics.

For example, antibacterial aminoglycosides such as gentamicin, streptomycins, kanamycins, tobramycins, and the like are known to have serious toxicity, particularly ototoxicity and nephrotoxicity, which reduce the value of such antimicrobials as therapeutic agents (see Goodman and Gilman's The Pharmacological Basis of Therapeutics, 6th ed., A. Goodman Gilman et al., eds; Macmillan Publishing Co., Inc., New York, 1980, pp. 1169-71).

Clearly, ototoxicity is a dose-limiting side-effect of antibiotic administration. Studies have shown that from 4% to 15% of patients receiving 1 gram per day for greater than 1 week develop measurable hearing loss, which slowly becomes worse and can lead to complete permanent deafness if treatment continues.

Nephrotoxicity and ototoxicity are serious dose-limiting side-effect for cisplatin, a platinum coordination complex, that has proven effective on a variety of human cancers including testicular, ovarian, bladder, and head and neck cancer. Cisplatin (Platinol®) damages auditory and vestibular systems. Salicylates, such as aspirin, are the most commonly used therapeutic drugs for their anti-inflammatory, analgesic, anti-pyretic and anti-thrombotic effects. Unfortunately, they too have ototoxic side effects and can lead to tinnitus ("ringing in the ears") and temporary hearing loss. Moreover, if the drug is used at high doses for a prolonged time, chronic and irreversible hearing impairment can become an issue. Another target organ for cisplatin toxicity is the kidney. This toxicity is manifested by reduced renal function and leads to serum electrolyte changes and pathological changes in the urine analysis. Doses of cisplatin, which produce changes in renal function may cause no histopathological changes. Higher doses of the drug lead to terstitial nephritis. Cisplatin also causes bone marrow hypoplasia, and can cause autonomic neuropathy. Slight changes in liver function and histopathology are also observed following cisplatin therapy.

Without being bound by theory, it is believed that cisplatin drugs and other potentially ototoxic drugs (such as aminoglycoside antibiotics) may induce the ototoxic effects via programmed cell death or apoptosis in inner ear tissue, particularly inner ear hair cells (Zhang et al., Neuroscience 2003, 120(1):191-205; Wang et al., J. Neuroscience 2003, 23(24): 8596-8607). In mammals, auditory hair cells are produced only during embryonic development and do not regenerate if lost during postnatal life, therefore, a loss of hair cells will result in profound and irreversible deafness. Unfortunately, at present, there are no effective therapies to treat the cochlea and reverse this condition. Thus, an effective therapy to prevent cell death of auditory hair cells would be of great therapeutic value.

Another type of hearing loss is presbycusis, which is age related hearing loss. It is estimated that about 30-35 percent of adults between the ages of 65 and 75 years and about 40-50 percent of people aged 75 and older have hearing loss. Accordingly, there exists a need for means to prevent, reduce or treat the incidence and/or severity of inner ear disorders and hearing impairments involving inner ear tissue, particularly inner ear hair cells.

By "exposure to an toxic agent" is meant that the toxic agent is made available to, or comes into contact with, a mammal. A toxic agent can be toxic to one or more organs in the body, for example, the ear, kidney, nervous system, liver and the like. Exposure to a toxic agent can occur by direct administration, e.g., by ingestion or administration of a food, medicinal, or therapeutic agent, e.g., a chemotherapeutic agent, by accidental contamination, or by environmental exposure, e.g., aerial or aqueous exposure.

Hearing loss relevant to the invention may be due to end-organ lesions involving inner ear hair cells, e.g., acoustic trauma, viral endolymphatic labyrinthitis, Meniere's disease. Hearing impairments include tinnitus, which is a perception of sound in the absence of an acoustic stimulus, and may be intermittent or continuous, wherein there is diagnosed a sensorineural loss. Hearing loss may be due to bacterial or viral infection, such as in herpes zoster oticus, purulent labyrinthitis arising from acute otitis media, purulent meningitis, chronic otitis media, sudden deafness including that of viral origin, e.g., viral endolymphatic labyrinthitis caused by viruses including mumps, measles, influenza, chicken pox, mononucleosis and adenoviruses. The hearing loss can be congenital, such as that caused by rubella, anoxia during birth, bleeding into the inner ear due to trauma during delivery, ototoxic drugs administered to the mother, erythroblastosis fetalis, and hereditary conditions including Waardenburg's syndrome and Hurler's syndrome.

The hearing loss can be noise-induced, generally due to a noise greater than about 85 decibels (db) that damages the inner ear. In a particular aspect of the invention, the hearing loss is caused by an ototoxic drug that effects the auditory portion of the inner ear, particularly inner ear hair cells. Incorporated herein by reference are chapters 196, 197, 198 and 199 of The Merck Manual of Diagnosis and Therapy, 14th Edition, (1982), Merck Sharp & Dome Research Laboratories, N.J. and corresponding chapters in the most recent 16th edition, including Chapters 207 and 210) relating to description and diagnosis of hearing and balance impairments.

It is the object of the present invention to provide a method and compositions for treating a mammal, to prevent, reduce, or treat a hearing impairment, disorder or imbalance, preferably an ototoxin-induced hearing condition, by administering to a mammal in need of such treatment a composition of the invention. One embodiment of the invention is a method for treating a hearing disorder or impairment wherein the ototoxicity results from administration of a therapeutically effective amount of an ototoxic pharmaceutical drug. Typical ototoxic drugs are chemotherapeutic agents, e.g. antineoplastic agents, and antibiotics. Other possible candidates include loop-diuretics, quinines or a quinine-like compound, and salicylate or salicylate-like compounds.

Ototoxic aminoglycoside antibiotics include but are not limited to neomycin, paromomycin, ribostamycin, lividomycin, kanamycin, amikacin, tobramycin, viomycin, gentamicin, sisomicin, netilmicin, streptomycin, dibekacin, fortimicin, and dihydrostreptomycin, or combinations thereof.

Particular antibiotics include neomycin B, kanamycin A, kanamycin B, gentamicin C1, gentamicin C1a, and gentamicin C2.

Ototoxic chemotherapeutic agents amenable to the methods of the invention include, but are not limited to an antineoplastic agent, including cisplatin or cisplatin-like compounds, taxol or taxol-like compounds, and other chemotherapeutic agents believed to cause ototoxin-induced hearing impairments, e.g., vincristine, an antineoplastic drug used to treat hematological malignancies and sarcomas. Cisplatin-like compounds include, inter alia, carboplatin (Paraplatin®), tetraplatin, oxaliplatin, aroplatin and transplatin.

The methods and compositions of the present invention are also effective in the treatment of acoustic trauma or mechanical trauma, preferably acoustic or mechanical trauma that leads to inner ear hair cell loss. Acoustic trauma to be treated in the present invention may be caused by a single exposure to an extremely loud sound, or following long-term exposure to everyday loud sounds above 85 decibels. Mechanical inner ear trauma to be treated in the present invention is for example the inner ear trauma following insertion and operation of an electronic device in the inner ear. The compositions of the present invention prevent or minimize the damage to inner ear hair cells associated with the device.

In some embodiments the composition of the invention is co-administered with an ototoxin. For example, the present invention provides an improved method for treatment of infection of a mammal receiving an antibiotic for treatment of the infection, comprising administering a therapeutically effective amount of one or more compounds (particularly novel siRNAs) which down-regulate expression of the mammalian pro-apoptotic gene, to the patient in need of such treatment to reduce or prevent ototoxin-induced hearing impairment associated with the antibiotic. The compounds, which down-regulate expression of a pro-apoptotic gene are preferably administered locally within the inner ear.

In yet another embodiment an improved method for treatment of cancer in a mammal by administration of a chemotherapeutic compound is provided, wherein the improvement comprises administering a therapeutically effective amount of a composition of the invention to the patient in need of such treatment to reduce or prevent ototoxin-induced hearing impairment associated with the chemotherapeutic drug. The compounds which reduce or prevent the ototoxin-induced hearing impairment, e.g. the novel siRNAs inter alia are preferably administered locally within the inner ear.

In another embodiment the methods of treatment are applied to treatment of hearing loss resulting from the administration of a chemotherapeutic agent in order to treat its ototoxic side effect.

In another embodiment the methods of the invention are applied to hearing impairments resulting from the administration of quinine and its synthetic substitutes, typically used in the treatment of malaria, to treat its ototoxic side-effect.

In another embodiment the methods of the invention are applied to hearing impairments resulting from administration of a diuretic to treat its ototoxic side effect. Diuretics, particularly "loop" diuretics, i.e. those that act primarily in the Loop of Henle, are candidate ototoxins. Illustrative examples, not limiting to the invention method, include furosemide, ethacrylic acid, and mercurials. Diuretics are typically used to prevent or eliminate edema. Diuretics are also used in non-edematous states for example hypertension, hypercalcemia, idiopathic hypercalciuria, and nephrogenic diabetes insipidus.

In one preferred embodiment, the compounds of the invention are used for treating acute renal failure, in particular acute renal failure due to ischemia in post surgical patients, and acute renal failure due to chemotherapy treatment such as cisplatin administration or sepsis-associated acute renal failure. A preferred use of the compounds of the invention is for the prevention of acute renal failure in high-risk patients undergoing major cardiac surgery or vascular surgery. The patients at high-risk of developing acute renal failure can be identified using various scoring methods such as the Cleveland Clinic algorithm or that developed by US Academic Hospitals (QMMI) and by Veterans' Administration (CICSS). Other preferred uses of the compounds of the invention are for the prevention of ischemic acute renal failure in kidney transplant patients or for the prevention of toxic acute renal failure in patients receiving chemotherapy.

In another preferred embodiment, the siRNA compounds of the invention are used for treating acute kidney injury in patients undergoing kidney transplantation. In one embodiment, the acute kidney injury is a result of kidney ischemia-reperfusion injury during kidney transplantation.

In one preferred embodiment, the siRNA compounds of the invention for treating acute kidney injury in patients undergoing kidney transplantation are siRNA compounds directed to the TP53 gene, more preferably the siRNA compound is the 15 compound having a sense sequence set forth in SEQ ID NO:2 and an antisense sequence set forth in SEQ ID NO:1.

The siRNA compounds of the invention for treating acute kidney injury in patients undergoing kidney transplantation are preferably administered intravenously, more preferably as a single slow intravenous push.

In one preferred embodiment, the siRNA compounds of the invention are used to treat patients undergoing deceased donor kidney transplant for prophylaxis of Delayed Graft Function. Delayed Graft Function is defined as the need for dialysis within the first seven days after kidney transplantation and is associated with poorer graft function and survival. The occurrence of Delayed Graft Function is significantly higher when the graft is obtained from a donor who died from brain or cardiac death, or when the graft has been kept in cold storage conditions for more than 24 h prior to transplantation (cold storage prior to transplantation).

In order to achieve prophylaxis of Delayed Graft Function following kidney transplantation, the siRNA compounds of the invention are administered to the recipient prior to the transplantation, and/or during the transplantation, and/or following the transplantation, preferably 1 min to 24 hours following revascularization of the graft in the recipient, more preferably 15 minutes to 4 hours following revascularization of the graft in the recipient. Preferred doses of the siRNA compounds of the invention are between 0.1-50 mg/kg, more preferably between 0.5-10 mg/kg. Additionally or alternatively, the siRNA compounds of the invention are administered to a living donor preferably 24 hours or less, most preferably one hour or less prior to harvest of the organ.

For kidney transplantation, either the donor or the recipient or both may be treated with a compound or composition of the present invention. Accordingly, the present invention relates to a method of treating a kidney donor or a kidney recipient comprising the step of administering to the donor or the recipient a therapeutically effective amount of a compound according to the present invention.

The invention further relates to a method for preserving a kidney transplant or graft comprising contacting the transplant or graft with an effective amount of compound of the present invention. Also provided is a method for reducing or preventing injury (in particular reperfusion injury) of a kidney transplant or graft during surgery and/or following removal of the organ from a subject comprising placing the kidney transplant or graft in an organ preserving solution wherein the solution comprises a compound according to the present invention.

In other embodiments the compounds and methods of the invention are useful for treating or preventing the incidence or severity of various diseases and conditions in a patient, in particular conditions which are result from ischemic/reperfusion injury or oxidative stress, ischemic optic neuropathy, dry eye syndrome, acute respiratory distress syndrome (ARDS) for example due to coronavirus infection or endotoxins, severe acute respiratory syndrome (SARS), and other acute lung injuries, ischemia reperfusion injury associated with organ transplantation such as kidney or lung transplantation, glaucoma, spinal cord injury, pressure sores, oral mucositis, osteoarthritis, chronic obstructive pulmonary disease (COPD) and chemical-induced toxicity. The methods comprising administering to the patient a composition comprising one or more inhibitors (such as siRNA compounds), which inhibit TP53; HTRA2; KEAP1; SHC1-SHC, ZNHIT1, LGALS3, and HI95 in a therapeutically effective dose, thereby treating the patient.

In other embodiments the compounds and methods of the invention are useful for treating or preventing the incidence or severity of other diseases and conditions in a patient. These diseases and conditions include stroke and stroke-like situations (e.g. cerebral, renal, cardiac failure), neuronal cell death, brain injuries with or without reperfusion, chronic degenerative diseases e.g. neurodegenerative disease including Alzheimer's disease, Huntington's disease, Parkinson's disease, multiple sclerosis, amyotrophic lateral sclerosis, spinobulbar atrophy, prion disease, Sjogren's Syndrome, and apoptosis resulting from traumatic brain injury (TBI).

The compounds and methods of the invention are directed to providing neuroprotection, cerebroprotection, and to prevent and/or treat cytotoxic T cell and natural killer cell-mediated apoptosis associated with autoimmune disease and transplant rejection, and to prevent cell death of cardiac cells including heart failure, cardiomyopathy, viral infection and bacterial infection of the heart, myocardial ischemia, myocardial infarct, and myocardial ischemia, coronary artery bypass graft, and to prevent and/or treat mitochondrial drug toxicity e.g. as a result of chemotherapy or HIV therapy, to prevent cell death during viral infection or bacterial infection, and to prevent and/or treat inflammation and inflammatory diseases, inflammatory bowel disease, sepsis and septic shock. Other uses include prevention of cell death from follicle to ovocyte stages, from ovocyte to mature egg stages and sperm (for example, methods of freezing and transplanting ovarian tissue, artificial fertilization), and to preserve fertility in mammals after chemotherapy, in particular human mammals, and to prevent and/or treat, macular degeneration, and to prevent and/or treat acute hepatitis, chronic active hepatitis, hepatitis-B, and hepatitis-C, and to prevent hair loss, (e.g. hair loss due- to male-pattern baldness, and hair loss due to radiation, chemotherapy or emotional stress), and to treat or ameliorate skin damage whereby the skin damage may be due to exposure to high levels of radiation, heat, chemicals, sun, or to burns and autoimmune diseases), and to prevent cell death of bone marrow cells in myelodysplastic syndromes (MDS), and to treat pancreatitis, and to treat rheumatoid arthritis, psoriasis, glomerulonephritis, atherosclerosis, and graft versus host disease (GVHD), and to treat retinal pericyte apoptosis, retinal damages resulting from ischemia, diabetic retinopathy, and to treat any disease states associated with overexpression of a pro-apoptotic gene, wherein the expression is associated with TP53, HTRA2; KEAP1; SHC1-SHC, ZNHIT1, LGALS3, and or HI95 expression.

The TP53 siRNA compounds of the present invention are particularly useful in the treatment of glaucoma and in ameliorating or treating the adverse effects of organ transplant, including ameliorating, treating or preventing perfusion injury.

For organ transplantation, either the donor or the recipient or both may be treated with a compound or composition of the present invention. Accordingly, the present invention relates to a method of treating an organ donor or an organ recipient comprising the step of administering to the organ donor or organ recipient a therapeutically effective amount of a compound according to the present invention.

The invention further relates to a method for preserving an organ comprising contacting the organ with an effective amount of compound of the present invention. Also provided is a method for reducing or preventing injury (in particular reperfusion injury) of an organ during surgery and/or following removal of the organ from a subject comprising placing the organ in an organ preserving solution wherein the solution comprises a compound according to the present invention.

The present invention also p ides for a process of preparing a pharmaceutical composition, which comprises:
  providing one or more double stranded compound of the invention; and
  admixing said compound with a pharmaceutically acceptable carrier.

In a preferred embodiment, the compound used in the preparation of a pharmaceutical composition is admixed with a carrier in a pharmaceutically effective dose. In a particular embodiment the compound of the present invention is conjugated to a steroid or to a lipid or to another suitable molecule e.g. to cholesterol.

Delivery

The siRNA molecules of the present invention may be delivered to the target tissue by direct application of the naked molecules prepared with a carrier or a diluent.

The term "naked siRNA" refers to siRNA molecules that are substantially free from any delivery vehicle that acts to assist, promote or facilitate entry into the cell, including viral sequences, viral particles, liposome formulations, lipofectin or precipitating agents and the like. For example, siRNA in PBS is "naked siRNA".

However, in some embodiments the siRNA molecules of the invention are delivered in liposome formulations and lipofectin formulations and the like and can be prepared by methods well known to those skilled in the art. Such methods are described, for example, in U.S. Pat. Nos. 5,593,972, 5,589, 466, and 5,580,859, which are herein incorporated by reference.

Delivery systems aimed specifically at the enhanced and improved delivery of siRNA into mammalian cells have been developed (see, for example, Shen et al FEBS Let. 539: 111-114 (2003), Xia et al., Nat. Biotech. 20: 1006-1010 (2002), Reich et al., Mol. Vision. 9: 210-216 (2003), Sorensen et al., J. Mol. Biol. 327: 761-766 (2003), Lewis et al., Nat. Gen. 32: 107-108 (2002) and Simeoni et al., NAR 31, 11: 2717-2724 (2003)). siRNA has recently been successfully used for inhibition of gene expression in primates; (for details see for example, Tolentino et al., Retina 24(1):132-138).

Respiratory formulations for siRNA are described in US patent application publication No. 2004/0063654. Cholesterol-conjugated siRNAs (and other steroid and lipid conjugated siRNAs) can been used for delivery (see for example Soutschek et al Nature 2004. 432: 173-177.; and Lorenz et al. Bioorg. Med. Chem. Lett. 14:4975-4977 (2004).

Pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art. In one specific embodiment of this invention topical and transdermal formulations may be selected. The siRNAs or pharmaceutical compositions of the present invention are administered and dosed in accordance with good medical practice, taking into account the clinical condition of the individual patient, the disease to be treated, the site and method of administration, scheduling of administration, patient age, sex, body weight and other factors known to medical practitioners. The compounds and compositions of the present invention may be administered alone or in combination with other pharmaceuticals. For example in transplant patients, it may be beneficial to co-administration of one or more compounds of the invention with an immunosuppressant, including cyclosporine, tacrolimus, azathioprine, prednisone and the like.

By "co-administration" is meant administration before, concurrently with, or after administration of an siRNA inhibitor as described above.

A "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art.

In general, the active dose of compound for humans is in the range of from 1 ng/kg to about 20-100 mg/kg body weight per day, preferably about 0.01 mg to about 2-10 mg/kg body weight per day, in a regimen of one dose per day or twice or three or more times per day for a period of 1-4 weeks or longer.

The compounds of the present invention can be administered by any of the conventional routes of administration. It should be noted that the compound can be administered as the compound or as pharmaceutically acceptable salt and can be administered alone or as an active ingredient in combination with pharmaceutically acceptable carriers, solvents, diluents, excipients, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. Liquid forms may be prepared for injection, the term including subcutaneous, transdermal, intravenous, intramuscular, intrathecal, and other parental routes of administration. The liquid compositions include aqueous solutions, with and without organic co-solvents, aqueous or oil suspensions, emulsions with edible oils, as well as similar pharmaceutical vehicles. In a particular embodiment, the administration comprises intravenous administration. In another embodiment the administration comprises topical or local administration In addition, in certain embodiments the compositions for use in the novel treatments of the present invention may be formed as aerosols, for example for intranasal administration.

The present invention further provides for a pharmaceutical composition comprising two or more siRNA molecules for the treatment of any of the diseases and conditions mentioned herein, whereby said two molecules may be physically mixed together in the pharmaceutical composition in amounts which generate equal or otherwise beneficial activity, or may be covalently or non-covalently bound, or joined together by a nucleic acid linker of a length ranging from 2-100, preferably 2-50 or 2-30 nucleotides. In one embodiment, the siRNA molecules are comprised of a double-stranded nucleic acid structure as described herein, wherein the two siRNA sequences are selected from SEQ ID NOS: 68-6815.

The siRNA molecules are covalently or non-covalently bound or joined by a linker to form a tandem siRNA molecule. Such tandem siRNA molecules comprising two siRNA sequences are typically of 38-150 nucleotides in length, more preferably 38 or 40-60 nucleotides in length, and longer accordingly if more than two siRNA sequences are included in the tandem molecule. A longer tandem molecule comprised of two or more longer sequences which encode siRNA produced via internal cellular processing, e.g., long dsRNAs, is also envisaged, as is a tandem molecule encoding two or more shRNAs. Such tandem molecules are also considered to be a part of the present invention. Particularly preferred tandem molecules are tandem molecules comprising one or two of the preferred siRNAs disclosed herein (the siRNAs, supra).

siRNA compounds that target any one of the pro-apoptotic genes disclosed herein may be the main active component in a pharmaceutical composition, or may be one active component of a pharmaceutical composition containing two or more siRNAs (or molecules which encode or endogenously produce two or more siRNAs, be it a mixture of molecules or one or more tandem molecules which encode two or more siRNAs), said pharmaceutical composition further being comprised of one or more additional siRNA molecule which targets one or more additional gene. Simultaneous inhibition of said additional gene(s) will likely have an additive or synergistic effect for treatment of the diseases disclosed herein.

Additionally, the siRNA compounds disclosed herein or any nucleic acid molecule comprising or encoding such siRNA can be linked or bound (covalently or non-covalently) to antibodies (including aptamer molecules) against cell surface internalizable molecules expressed on the target cells, in order to achieve enhanced targeting for treatment of the diseases disclosed herein. For example, anti-Fas antibody (preferably a neutralizing antibody) may be combined (covalently or non-covalently) with siRNA. In another example, an aptamer which can act like a ligand/antibody may be combined (covalently or non-covalently) with any siRNA to a pro-apoptotic gene disclosed herein.

The compounds of the present invention can be delivered either directly or with viral or non-viral vectors. When delivered directly the sequences are generally rendered nuclease resistant. Alternatively the sequences can be incorporated into expression cassettes or constructs such that the sequence is expressed in the cell as discussed herein below. Generally the construct contains the proper regulatory sequence or promoter to allow the sequence to be expressed in the targeted cell. Vectors optionally used for delivery of the compounds of the present invention are commercially available, and may be modified for the purpose of delivery of the compounds of the present invention by methods known to one of skill in the art.

It is also envisaged that a long oligonucleotide (typically 25-500 nucleotides in length) comprising one or more stem and loop structures, where stem regions comprise the sequences of the oligonucleotides of the invention, may be delivered in a carrier, preferably a pharmaceutically acceptable carrier, and may be processed intracellularly by endogenous cellular complexes (e.g. by DROSHA and DICER as described above) to produce one or more smaller double stranded oligonucleotides (siRNAs) which are oligonucleotides of the invention. This oligonucleotide can be termed a tandem shRNA construct. It is envisaged that this long oligonucleotide is a single stranded oligonucleotide comprising one or more stem and loop structures, wherein each stem region comprises a sense and corresponding antisense siRNA sequence of the pro-apoptotic genes of the invention. In particular, it is envisaged that this oligonucleotide comprises sense and antisense siRNA sequences as depicted in SEQ ID NOS:68-6815.

Although the inhibitor may be an siRNA molecule, other inhibitors contemplated to be used in the methods of the invention to inhibit expression of a pro-apoptotic gene and to treat the diseases and conditions described herein are inter alia antibodies, preferably neutralizing antibodies or fragments thereof, including single chain antibodies, antisense oligonucleotides, antisense DNA or RNA molecules, ribozymes, proteins, polypeptides and peptides including peptido-mimetics and dominant negatives, and also expression vectors expressing all the above. Additional inhibitors may be small chemical molecules, which generally have a molecular weight of less than 2000 daltons, preferably less than 1000 daltons, more preferably less than 500 daltons. These inhibitors may act as follows: small molecules may affect expression and/or activity; antibodies may affect activity; all kinds of antisense may affect gene expression; and dominant negative polypeptides and peptidomimetics may affect activity; expression vectors may be used inter alia for delivery of antisense or dominant-negative polypeptides or antibodies.

Antibodies

The term "antibody" refers to IgG, IgM, IgD, IgA, and IgE antibody, inter alia. The definition includes polyclonal antibodies or monoclonal antibodies. This term refers to whole antibodies or fragments of antibodies comprising an antigen-binding domain, e.g. antibodies without the Fc portion, single chain antibodies, miniantibodies, fragments consisting of essentially only the variable, antigen-binding domain of the antibody, etc. The term "antibody" may also refer to antibodies against polynucleotide sequences obtained by cDNA vaccination. The term also encompasses antibody fragments which retain the ability to selectively bind with their antigen or receptor and are exemplified as follows, inter alia:

(1) Fab, the fragment which contains a monovalent antigen-binding fragment of an antibody molecule which can be produced by digestion of whole antibody with the enzyme papain to yield a light chain and a portion of the heavy chain;

(Fab')$_2$, the fragment of the antibody that can be obtained by treating whole antibody with the enzyme pepsin without subsequent reduction; F(ab'$_2$) is a dimer of two Fab fragments held together by two disulfide bonds;

(3) Fv, defined as a genetically engineered fragment containing the variable region of the light chain and the variable region of the heavy chain expressed as two chains; and (4) Single chain antibody (SCA), defined as a genetically engineered molecule containing the variable region of the light chain and the variable region of the heavy chain linked by a suitable polypeptide linker as a genetically fused single chain molecule.

Antisense Molecules

By the term "antisense" (AS) or "antisense fragment" is meant a polynucleotide fragment (comprising either deoxyribonucleotides, ribonucleotides or a mixture of both) having inhibitory antisense activity, said activity causing a decrease in the expression of the endogenous genomic copy of the corresponding gene. An AS polynucleotide is a polynucleotide which comprises consecutive nucleotides having a sequence of sufficient length and homology to a sequence present within the sequence of the target gene to permit hybridization of the AS to the gene. Many reviews have covered the main aspects of antisense (AS) technology and its therapeutic potential (Aboul-Fadl T., Curr Med. Chem. 2005, 12(19):2193-214; Crooke S T, Curr Mol. Med. 2004, 4(5): 465-87; Crooke S T, Ann Rev Med. 2004, 55:61-95; Vacek M et al., Cell Mol Life Sci. 2003, 60(5):825-33; Cho-Chung Y S, Arch Pharm Res. 2003, 26(3):183-91. There are further reviews on the chemical (Crooke et al., Hematol Pathol. 1995, 9(2):59-72), cellular (Wagner, Nature. 1994, 372(6504):333-5) and therapeutic (Scanlon, et al, FASEB J. 1995, 9(13): 1288-96) aspects of AS technology. Antisense intervention in the expression of specific genes can be achieved by the use of modified AS oligonucleotide sequences (for recent reports see Lefebvre-d'Hellencourt et al, 1995; Agrawal, 1996; Lev-Lehman et al, 1997).

AS oligonucleotide sequences may be short sequences of DNA, typically 15-30 mer but may be as small as 7-mer (Wagner et al, Nat. Biotech. 1996, 14(7):840-4), designed to complement a target mRNA of interest and form an RNA:AS duplex. This duplex formation can prevent processing, splicing, transport or translation of the relevant mRNA. Moreover, certain AS nucleotide sequences can elicit cellular RNase H activity when hybridized with their target mRNA, resulting in mRNA degradation (Calabretta et al, Semin Oncol. 1996, 23(1):78-87). In that case, RNase H will cleave the RNA component of the duplex and can potentially release the AS to further hybridize with additional molecules of the target RNA. An additional mode of action results from the interaction of AS with genomic DNA to form a triple helix, which can be transcriptionally inactive.

The sequence target segment for the antisense oligonucleotide is selected such that the sequence exhibits suitable energy related characteristics important for oligonucleotide duplex formation with their complementary templates, and shows a low potential for self-dimerization or self-complementation (Anazodo et al., 1996, Biochem. Biophys. Res. Comm. 229:305-309). For example, the computer program OLIGO (Primer Analysis Software, Version 3.4), can be used to determine antisense sequence melting temperature, free energy properties, and to estimate potential self-dimer formation and self-complimentary properties. The program allows the determination of a qualitative estimation of these two parameters (potential self-dimer formation and self-complimentary) and provides an indication of "no potential" or "some potential" or "essentially complete potential". Using this program target segments are generally selected that have estimates of no potential in these parameters. However, segments can be used that have "some potential" in one of the categories. A balance of the parameters is used in the selection as is known in the art. Further, the oligonucleotides are also selected as needed so that analog substitution does not substantially affect function.

Phosphorothioate antisense oligonucleotides do not normally show significant toxicity at concentrations that are effective and exhibit sufficient pharmacodynamic half-lives in animals (Agrawal, et al., PNAS USA. 1997, 94(6):2620-5) and are nuclease resistant. Antisense oligonucleotide inhibition of basic fibroblast growth factor (bFGF), having mitogenic and angiogenic properties, suppressed 80% of growth in glioma cells (Morrison, J Biol. Chem. 1991 266(2):728-34) in a saturable and specific manner. Being hydrophobic, antisense oligonucleotides interact well with phospholipid membranes (Akhter et al., NAR. 1991, 19:5551-5559). Following their interaction with the cellular plasma membrane, they are actively (or passively) transported into living cells (Loke et al., PNAS 1989, 86(10):3474-8), in a saturable mechanism predicted to involve specific receptors (Yakubov et al., PNAS, 1989 86(17):6454-58).

Ribozymes

A "ribozyme" is an RNA molecule that possesses RNA catalytic ability (see Cech for review) and cleaves a specific site in a target RNA. In accordance with the present invention, ribozymes which cleave mRNA may be utilized as inhibitors. This may be necessary in cases where antisense therapy is limited by stoichiometric considerations (Sarver et al., 1990, Gene Regulation and Aids, pp. 305-325). Ribozymes can then be used that will target the a gene associated with a bone marrow disease. The number of RNA molecules that are cleaved by a ribozyme is greater than the number predicted by stoichiometry. (Hampel and Tritz, Biochem. 1989, 28(12): 4929-33; Uhlenbeck, Nature. 1987. 328(6131):596-600).

Ribozymes catalyze the phosphodiester bond cleavage of RNA. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (U.S. Pat. No. 5,225,347). The latter two families are derived from viroids and virusoids, in which the ribozyme is believed to separate monomers from oligomers created during rolling circle replication (Symons, 1989 and 1992). Hammerhead and hairpin ribozyme motifs are most commonly adapted for trans-cleavage of mRNAs for gene therapy (Sullivan, 1994). In general the ribozyme has a length of from about 30-100 nucleotides. Delivery of ribozymes is similar to that of AS fragments and/or siRNA molecules.

Screening for Inhibitors of Pro-Apoptotic Gene Expression

Some of the compounds and compositions of the present invention may be used in a screening assay for identifying and isolating compounds that modulate the activity of a pro-apoptotic gene, in particular compounds that modulate a disorder accompanied by an elevated level of a pro-apoptotic gene. The compounds to be screened comprise inter alia substances such as small chemical molecules and antisense oligonucleotides.

The inhibitory activity of the compounds of the present invention on a pro-apoptotic gene or binding of the compounds of the present invention to a pro-apoptotic gene or mRNA may be used to determine the interaction of a test compound with the sequence e.g., if the test compound competes with the oligonucleotides of the present invention for inhibition of a pro-apoptotic gene, or if the additional compound rescues said inhibition. The inhibition or activation can be tested by various means, such as, inter alia, assaying for the product of the activity of a pro-apoptotic polypeptide (such as downstream polypeptides which are regulated by the pro-apoptotic polypeptide) or displacement of binding compound from the pro-apoptotic polypeptide in radioactive or fluorescent competition assays.

The present invention is illustrated in detail below with reference to Examples, but is not to be construed as being limited thereto.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

General Methods in Molecular Biology

Standard molecular biology techniques known in the art and not specifically described were generally followed as in Sambrook et al., Molecular Cloning: A Laboratory Manual, Cold Spring Harbor Laboratory Press, New York (1989), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683, 202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In situ PCR in combination with Flow Cytometry can be used for detection of cells containing specific DNA and mRNA sequences (Testoni et al., 1996, Blood 87:3822). Methods of performing RT-PCR are also well known in the art.

Example 1

In Vitro Testing of the siRNA Compounds for Pro-Apoptotic Genes

General: About $1.5-2 \times 10^5$ tested cells (HeLa cells or 293T cells for siRNA targeted the human gene and NRK52 cells or NMUMG cells for siRNA targeted the rat/mouse gene) were seeded per well in 6 wells plate (70-80% confluent).

At 24 h subsequently, cells were transfected with siRNA compounds using Lipofectamine® 2000 reagent (Invitrogene) at final concentration of 500 pM, 5 nM, 20 nM or 40 nM. The cells were incubated at 37° C. in a $CO_2$ incubator for 72 h.

As positive control for cells transfection PTEN-Cy3 labeled siRNA compounds were used. As negative control for siRNA activity GFP siRNA compounds were used.

At 72 h after transfection cells were harvested and RNA was extracted from cells. Transfection efficiency was tested by fluorescent microscopy.

Results: The percent of inhibition of gene expression using specific preferred siRNAs was determined using qPCR analysis of target gene in cells expressing the endogenous gene. The data demonstrate the percent of knockdown of the expression of the target gene in cells. In general, the siRNAs having specific sequences that were selected for in vitro testing were specific for both human and the rat/rabbit genes. Similar results of reduced expression of specific genes are obtained with other siRNAs, the sequences of which are listed in SEQ ID NOS:68-6815.

TABLE 2

Percent of knockdown of the expression of selected genes in cells using 19-mer siRNA molecules.

| SiRNA tested | SEQ ID NO | sense seq 5'>3' | SEQ ID NO | anti-sense seq 5'>3' | % of control** |
|---|---|---|---|---|---|
| HTRA2_11 | 14 | GAAUCACAGAAACACUUUU | 15 | AAAAGUGUUUCUGUGAUUC | 18, 18 |
| HTRA2_13 | 16 | CCGUGGUCUAUAUCGAGAU | 17 | AUCUCGAUAUAGACCACGG | 11, 15 |
| HTRA2_16 | 18 | GCCGUGGUCUAUAUCGAGA | 19 | UCUCGAUAUAGACCACGGC | 27 |
| HTRA2_18 | 20 | CAGCUAUUGAUUUUGGAAA | 21 | UUUCCAAAAUCAAUAGCUG | 17, 11, 15 |
| HTRA2_21 | 22 | GCUAUUGAUUUUGGAAACU | 23 | AGUUUCCAAAAUCAAUAGC | 15, 14, 9 |
| HTRA2_22 | 24 | AGCUAUUGAUUUUGGAAAC | 25 | GUUUCCAAAAUCAAUAGCU | 19, 10, 8 |
| KEAP1_2 | 26 | GCCUCAUUGAAUUCGCCUA | 27 | UAGGCGAAUUCAAUGAGGC | 18, 32 |
| KEAP1_8 | 28 | GGGCAAAAAUACAGUCCAA | 29 | UUGGACUGUAUUUUUGCCC | 18, 7 (5 nM) |
| KEAP1_9 | 30 | GGAGUAUCAUUGUUUUUGU | 31 | ACAAAAACAAUGAUACUCC | 8, 7 |
| KEAP1_10 | 32 | GGCAAAAAUACAGUCCAAU | 33 | AUUGGACUGUAUUUUUGCC | 15, 6 (5 nM) |
| KEAP1_11 | 34 | CACCAUGUGAUUUAUUCUU | 35 | AAGAAUAAAUCACAUGGUG | 24 (5 nM) |
| KEAP1_12 | 36 | ACUGCAAAUAACCCAUCUU | 37 | AAGAUGGGUUAUUUGCAGU | 38, 12 (5 nM) |
| KEAP1_13 | 38 | CACUGCAAAUAACCCAUCU | 39 | AGAUGGGUUAUUUGCAGUG | 37 |
| KEAP1_14 | 40 | GCAGCUGUCACCAUGUGAU | 41 | AUCACAUGGUGACAGCUGC | 24 |
| SHC1_1 | 42 | ACCUGAAAUUUGCUGGAAU | 43 | AUUCCAGCAAAUUUCAGGU | 16, 12 (5 nM) |
| SHC1_2 | 44 | CAGAGAGCUUUUUGAUGAU | 45 | AUCAUCAAAAAGCUCUCUG | 5, 13 |
| SHC1_3 | 46 | CACAUGCAAUCUAUCUCAU | 47 | AUGAGAUAGAUUGCAUGUG | 21, 12 |
| ZNHIT1_1 | 48 | CCGAGGUGAUCAUUUUAAA | 49 | UUUAAAAUGAUCACCUCGG | 8, 14 |
| ZNHIT1_2 | 50 | GUGACCACAUCUUUAAAAU | 51 | AUUUUAAAGAUGUGGUCAC | 22 |
| ZNHIT1_10 | 52 | CUGGAAAGAAAAAGAAGAA | 53 | UUCUUCUUUUUCUUUCCAG | 18 |
| ZNHIT1_11 | 54 | ACACUGGAAAGAAAAAGAA | 55 | UUCUUUUUCUUUCCAGUGU | 20 |
| LGALS3_12 | 56 | GUGCCUUAUAACCUGCCUU | 57 | AAGGCAGGUUAUAAGGCAC | 32, 51 |
| LGALS3_13 | 58 | GGAAGAAAGACAGUCGGUU | 59 | AACCGACUGUCUUUCUUCC | 18, 29, 27 |
| LGALS3_14 | 60 | GCAGUACAAUCAUCGGGUU | 61 | AACCCGAUGAUUGUACUGC | 26, 51 |
| LGALS3_15 | 62 | GAGAGUCAUUGUUUGCAAU | 63 | AUUGCAAACAAUGACUCUC | 24, 29, 13 |
| LGALS3_18 | 64 | GGGUUAAAAAACUCAAUGA | 65 | UCAUUGAGUUUUUUAACCC | 14, 30 |

**% of control in separate tests using 20 nM concentration of siRNA molecules (unless indicated otherwise).
All sequences are presented in a 5'-3' orientation.

Example 2

Model Systems of Acute Renal Failure (ARF)

ARF is a clinical syndrome characterized by rapid deterioration of renal function that occurs within days. Without being bound by theory the acute kidney injury may be the result of renal ischemia-reperfusion injury such as renal ischemia-reperfusion injury in patients undergoing major surgery such as major cardiac surgery. The principal feature of ARF is an abrupt decline in glomerular filtration rate (GFR), resulting in the retention of nitrogenous wastes (urea, creatinine). Recent studies support the hypothesis that apoptosis in renal tissues is prominent in most human cases of ARF. The principal site of apoptotic cell death is the distal nephron. During the initial phase of ischemic injury, loss of integrity of the actin cytoskeleton leads to flattening of the epithelium, with loss of the brush border, loss of focal cell contacts, and subsequent disengagement of the cell from the underlying substratum.

Testing the active siRNA for each pro-apoptotic gene separately for treating ARF is done using an animal model for ischemia-reperfusion-induced ARF.

Ischemia-reperfusion induced ARF: Ischemia-reperfusion injury is induced in rats following 45 minutes bilateral kidney arterial clamp and subsequent release of the clamp to allow 24 hours of reperfusion. Twelve mg/kg of siRNA of the invention (i.e. siRNA to a specific pro-apoptotic gene) are injected into the jugular vein 30 minutes prior to and 4 hours following the clamp. ARF progression is monitored by measurement of serum creatinine levels before (baseline) and 24 hrs post surgery. At the end of the experiment, the rats are perfused via an indwelling femoral line with warm PBS followed by 4% paraformaldehyde. The left kidneys are removed and stored in 4% paraformaldehyde for subsequent histological analysis. Acute renal failure is frequently defined as an acute increase of the serum creatinine level from baseline. An increase of at least 0.5 mg per dL or 44.2 μmol per L of serum creatinine is considered as an indication for acute renal failure. Serum creatinine is measured at time zero before the surgery and at 24 hours post ARF surgery. The results show that the siRNA compounds of the invention prevent onset of acute renal failure in this model.

Example 3

Model Systems of Pressure Sores or Pressure Ulcers

Pressure sores or pressure ulcers including diabetic ulcers, are areas of damaged skin and tissue that develop when sustained pressure (usually from a bed or wheelchair) cuts off circulation to vulnerable parts of the body, especially the skin on the buttocks, hips and heels. The lack of adequate blood flow leads to ischemic necrosis and ulceration of the affected tissue. Pressure sores occur most often in patients with diminished or absent sensation or who are debilitated, emaciated, paralyzed, or long bedridden. Tissues over the sacrum, ischia, greater trochanters, external malleoli, and heels are especially susceptible; other sites may be involved depending on the patient's situation.

Testing the active inhibitors of the invention (such as siRNA) for treating pressure sore, ulcers and similar wounds is performed in the mouse model described in Reid et al., Cyclical Magnetic Pressure Necrosis: J Surgical Research 2004, 116: 172-180. Additionally, rabbit models described by Mustoe et al, JCI, 1991 87(2):694-703; Ahn & Mustoe, Ann Plas Surg, 1991 24(1):17-23 are used for testing the siRNAs of the invention. The results show that the siRNA compounds treat and prevent pressure sores, ulcers and similar wounds.

Example 4

Model Systems of Chronic Obstructive Pulmonary Disease (COPD)

Chronic obstructive pulmonary disease (COPD) is characterized mainly by emphysema, which is permanent destruction of peripheral air spaces, distal to terminal bronchioles. Emphysema is also characterized by accumulation of inflammatory cells such as macrophages and neutrophils in bronchioles and alveolar structures. Emphysema and chronic bronchitis may occur as part of COPD or independently and involve apoptosis.

Testing the active inhibitors of the invention (such as siRNA) for treating COPD/emphysema/chronic bronchitis is done in the following animal models:
Cigarette smoke-induced emphysema model: chronic exposure to cigarette smoke causes emphysema in several animals such as, inter alia, mouse, guinea pig.
Lung protease activity as a trigger of emphysema.
VEGFR inhibition model of emphysema.
Bronchial instillation with human neutrophil/pancreatic elastase in rodents.
MMP (matrix metalloprotease)-induced emphysema.
Inflammation-induced emphysema.

These models and others are described in co-assigned PCT patent application WO 2006/023544, and PCT/IL2008/ 000522 which are hereby incorporated by reference into this application. The siRNA compounds of the invention prevent formation of emphysema.

Example 5

Model Systems of Spinal Cord Injury

Spinal cord injury, or myelopathy, is a disturbance of the spinal cord that results in loss of sensation and/or mobility. The two common types of spinal cord injury are due to trauma and disease. Traumatic injury can be due to automobile accidents, falls, gunshot, diving accidents inter alia, and diseases which can affect the spinal cord include polio, spina bifida, tumors and Friedreich's ataxia.
Uptake of siRNA Molecules into Neurons Following Injection into Injured Spinal-Cord:
The uptake of Cy3 labeled siRNA (delivered by injection into the injured cord) in different types of cells was examined following spinal cord contusion in 18 rats and in uninjured rats (9 rats). Sagittal cryosections were produced and immunostaining using four different groups of antibodies was performed in order to determine whether uptake has occurred in neurons, astroglia, oligdendroglia and/or macrophages/microglia. Markers for neurons were NeuN, or GAP43; markers for astroglia and potential neural stem cells were GFAP, nestin or vimentin; markers for oligdendroglia were NG2 or APC; markers for macrophages/microglia were ED1 or Iba-1 (Hasegawa et al., 2005. Exp Neurol 193 394-410).

Six rats were injected with two different doses of Cy3 labeled siRNA (1 μg/μl, 10 μg/μl) and were left for 1 and 3 days before sacrifice. Histological analyses indicate that many long filamentous profiles have taken up the labeled siRNA as well as other processes and cell bodies. Immunostaining with antibodies to MAP2 has identified uptake of label into dendrites and into cell bodies of neurons including motoneurons. Staining with other antibodies specific to astrocytes or macrophages revealed lower uptake of Cy3 labeled siRNA as compared to neurons. These results indicate that siRNA molecules injected to the injured spinal-cord reach the cell body and dendrites of neurons including motoneurons.
The Spinal-Cord Injury Animal Model:
Adult female Sprague-Dawley rats are anesthetized with 40 mg/kg of pentobarbital and the spinal thoracic T9-10 is exposed by laminectomy. Contusive injury are produced by dropping a 10 gm rod onto the exposed spinal cord from a height of 12.5 mm using MASCIS (Multicenter Animal Spinal Cord Injury Study) impactor (as described In Basso et al., Journal of Neurotrauma Vol 12 (1), p 1-21 1995 and in Basso et al., Journal of Neurotrauma Vol 13 (7), p 343-59 1996). Prior to injury, three point injections of the tested siRNA are performed at the injury epicenter 2 mm rostral and caudal to the epicenter. GFP siRNA is injected in additional five rats as a control. Each injection is conducted slowly during a period of 10 min into dorsal column (~1 mm depth) of 110 using a Hamilton syringe. Following injections, muscles and skin are closed separately. The behavioral assessment of the recovery following the spinal cord contusion is preformed using an open field locomotor test as described by Basso et al (the BBB locomotor rating scale).

Instead of using direct injection to the spinal cord, it is possible to deliver the siRNA molecules to the spinal-cord by using intrathecal delivery (such as using Alzet pump).

siRNA according to SEQ ID NOS: 68-6815 are tested in this animal model and the results show that these siRNA compounds treat and/or prevent spinal-cord injury.

Example 6

Model Systems of Glaucoma and Ischemic Optic Neuropathy

Testing the active siRNA of the invention for treating or preventing glaucoma is preformed in rat animal model for optic nerve crush described for example in: Kazumi Maeda et al., "A Novel Neuroprotectant against Retinal Ganglion Cell Damage in a Glaucoma Model and an Optic Nerve Crush Model in the Rat", Investigative Ophthalmology and visual Science (IOVS), March 2004, Vol. 45, No. 3. Specifically, for optic nerve transection the orbital optic nerve (ON) of anesthetized rats is exposed through a supraorbital approach, the meninges severed and all axons in the ON transected by crushing with forceps for 10 seconds, 2 mm from the lamina cribrosa.

siRNA compounds of the invention are tested in this animal model and the results show that these siRNA compounds treat and/or prevent glaucoma.

Other animal models for glaucoma and ischemic optic neuropathy for testing the siRNA compounds of the invention are as following:

For axotomy model: Pawel Kermer et al., "Transection of the optic nerve in rats: studying neuronal death and survival in vivo". Brain Research Protocols 7 (2001) 255-260.

For optic ischemia reperfusion model: Akitaka Tsujikawa et al., "In Vivo Evaluation of Leukocyte Dynamics in Retinal Ischemia Reperfusion Injury", Investigative Ophthalmology and visual Science (IOVS), April 1998, Vol. 39, No. 5.

For elevated intraocular pressure model: Morrison, J C et al., "A rat model of chronic pressure-induced optic nerve damage". (1997) Exp Eye Res 64,85-96.

For pharmacological ischemia reperfusion model: Koichi Masuzawa et al., "A Model of Retinal Ischemia-Reperfusion Injury in Rats by Subconjunctival Injection of Endothelin-1". Exp. Biol. Med. 2006 June; 231(6):1085-9.

Example 7

Model Systems of Ischemia Reperfusion Injury Following Lung Transplantation in Rats Lung ischemia/reperfusion injury is achieved in a rat animal model as described in Teruaki Mizobuchi et al., The Journal of Heart and Lung Transplantation, Vol 23 No. 7 (2004) and in Kazuhiro Yasufuku et al., Am. J. Respir. Cell Mol Biol, Vol 25, pp 26-34 (2001).

Specifically, after inducing anesthesia with isoflurane, the trachea is cannulated with a 14-gauge Teflon catheter and the rat is mechanically ventilated with rodent ventilator using 100% oxygen, at a rate of 70 breaths per minute and 2 cm $H_2O$ of positive end-respiratory pressure. The left pulmonary artery, veins and main stem bronchus are occluded with a Castaneda clamp. During the operation, the lung is kept moist with saline and the incision is covered to minimize evaporative losses. The period of ischemia is 60 minutes long. At the end of the ischemic period the clamp is removed and the lung is allowed to ventilate and reperfuse for further 4 h, 24 h, and 5 d post induction of lung ischemia. At the end of the experiment, the lungs are gently harvested and either frozen for RNA extraction or fixed in glutaraldehyde cocktail for subsequent histological analysis.

siRNA compounds of the invention are tested in this animal model and the results show that these siRNA compounds treat and/or prevent ischemia reperfusion injury following lung transplantation.

Example 8

Model Systems of Acute Respiratory Distress Syndrome

The active siRNA compounds of the invention are tested in an animal model for acute respiratory distress syndrome as described, for example, by Chen, et al. J Biomed Sci. 2003; 10(6 Pt 1):588-92).

The results show that these siRNA compounds can treat and/or prevent acute respiratory distress syndrome.

Example 9

Model Systems of Hearing Loss Conditions (i) Distribution of Cy3-PTEN siRNA in the Cochlea Following Local Application to the Round Window of the Ear:

A solution of 1 µg/100 µl of Cy3-PTEN siRNA (total of 0.3-0.4 µg) PBS was applied to the round window of chinchillas. The Cy3-labelled cells within the treated cochlea were analyzed 24-48 hours post siRNA round window application after sacrifice of the chinchillas. The pattern of labeling within the cochlea was similar following 24 h and 48 h and includes labeling in the basal turn of cochlea, in the middle turn of cochlea and in the apical turn of cochlea. Application of Cy3-PTEN siRNA onto scala tympani revealed labeling mainly in the basal turn of the cochlea and the middle turn of the cochlea. The Cy3 signal is persistent to up to 15 days after the application of the Cy3-PTEN siRNA. These results indicate for the first time that local application of siRNA molecules within the round window leads to significant penetration of the siRNA molecules to the basal, middle and apical turns of the cochlea. The active siRNAs of the invention are tested in this model.

(ii) Animal Model of Carboplatin-Induced or Cisplatin-Induced Hair Cell Death in the Cochlea of Chinchilla:

Chinchillas are pre-treated by direct administration of specific QM5 siRNA (sense strand: GAAGAAAAUUUCCG-CAAAA (SEQ ID NO:66); antisense strand: UUUUGCG-GAAAUUUUCUUC (SEQ ID NO:67) in saline to the left ear of each animal. Saline is given to the right ear of each animal as placebo. Two days following the administration of the specific siRNA, the animals are treated with carboplatin (75 mg/kg ip) or cisplatin (intraperitoneal infusion of 13 mg/kg over 30 minutes). After sacrifice of the chinchillas (two weeks post carboplatin treatment) the % of dead cells of inner hair cells (IHC) and outer hair cells (OHC) is calculated in the left ear (siRNA treated) and in the right ear (saline treated). The results show that the siRNA compounds prevent cell death of inner hair cells (iii) Animal Model of Acoustic-Induced Hair Cell Death in the Cochlea of Chinchilla:

The activity of specific siRNA compounds to each pro-apoptotic gene described herein in an acoustic trauma model is studied in chinchilla. The animals are exposed to an octave band of noise centered at 4 kHz for 2.5 h at 105 dB. The left ear of the noise-exposed chinchillas is pre-treated (48 h before the acoustic trauma) with 30 µg of siRNA in ~10 µL of saline; the right ear is pre-treated with vehicle (saline). The compound action potential (CAP) is a convenient and reliable electrophysiological method for measuring the neural activity transmitted from the cochlea. The CAP is recorded by placing an electrode near the base of the cochlea in order to detect the local field potential that is generated when a sound stimulus, such as click or tone burst, is abruptly turned on. The functional status of each ear is assessed 2.5 weeks after the acoustic trauma. Specifically, the mean threshold of the compound action potential recorded from the round window is determined 2.5 weeks after the acoustic trauma in order to determine if the thresholds in the siRNA-treated ear are lower (better) than the untreated (saline) ear. In addition, the amount of inner and outer hair cell loss is determined in the siRNA-treated and the control ear.

The results show that there is less cell death of inner and outer hair cells in the siRNA-treated ear than the control ear.

Example 10

Model Systems of Dry Eve

Mouse and Rat Models for Lacrimal Inflammation (Dacryoadenitis):
1. The nonobese diabetic (NOD) mouse model. Male NOD mice show significant inflammatory lesions of the lacrimal gland from the age of 8 weeks.
2. The MRL/MpJ-fas_/fas_(MRL/_) and MRL/MpJ-faslpr/faslpr (MRL/lpr) mouse models of Sjogren's syndrome (see in Jabs, D A, Enger, C, Prendergast, R A (1991) Murine models of Sjögren's syndrome: evolution of the lacrimal gland inflammatory lesions *Invest Ophthalmol Vis Sci* 32,371-380) exhibit lacrimal gland infiltrates characterized by a predominance of CD4 T cells. The extent of the lacrimal gland inflammation is significantly greater in lacrimal glands of female MRL/_and MRL/lpr mice.
3. The IQI/Jic has recently been established as a new mouse model for primary Sjogren's syndrome (see in J. Biol. Chem., Vol. 280, Issue 5, 3982-3988, Autoimmunity against a Tissue Kallikrein in IQI/Jic *Mice A MODEL FOR SJÖGREN'S SYNDROME Kensuke Takada, Mitsuyoshi Takiguchi, Akihiro Konno, and Mutsumi Inaba). The lymphocytic infiltration is well restricted to salivary and lacrimal glands.*
4. Rat model: experimental immune dacryoadenitis may be produced also in Lewis rats by sensitization with a single intradermal administration of an extract of lacrimal gland in complete Freund's adjuvant (cfa) and simultaneous intravenous injection of killed *bordetella pertussis*. (see in: Invest Ophthalmol Vis Sci. 1987 February; 28(2):276-80. Experimental autoimmune dacryoadenitis. II. Harderian gland disease in the rat. Liu S H, Sakai F, Prendergast R A, Silverstein A M).
Models for Evaporative Dry Eye:
See in: Ann N Y Acad. Sci. 2002 June; 966:211-22. Androgen deficiency, Meibomian gland dysfunction, and evaporative dry eye. Sullivan D A, Sullivan B D, Evans J E, Schirra F, Yamagami H, Liu M, Richards S M, Suzuki T, Schaumberg D A, Sullivan R M, Dana M R.

The tear film is constantly exposed to multiple environmental factors, including variable temperatures, airflow, and humidity, which may stimulate or retard its evaporation. The lipids produced by the Meibomian glands and spread onto the aqueous phase by the shear forces produced by each blink, protect the tear film from excessive evaporation. Short-term models for hyperevaporative dry eye have been created by preventing rabbits from blinking through placement of lid specula or sutures. After 2 hours of desiccation induced by lid specula, dry spots appear on the rabbit corneal epithelial surface and stain with methylene blue.

siRNA compounds of the invention are tested in the above animal model systems and the results show that these siRNA compounds treat and/or prevent dry eye symptoms.

Example 11

Model Systems for Transplantation-Associated Acute Kidney Injury

Warm Ischemia—
A left nephrectomy was performed, followed by auto transplantation that resulted in a warm kidney graft preservation period of 45 minutes. Following auto transplantation, a right nephrectomy was performed on the same animal. An anti-TP53 gene siRNA, QM5 siRNA, (sense strand: GAA-GAAAAUUUCCGCAAAA (SEQ ID NO:66); antisense strand: UUUUGCGGAAAUUUUCUUC (SEQ ID NO:67) was administered intravenously via the femoral vein either before harvesting of the kidney graft (mimicking donor treatment) ("pre"), or after the kidney autotransplantation (mimicking recipient treatment), or both before harvest and after transplantation (combined donor and recipient treatment) ("pre-post").

Cold Ischemia—
A left nephrectomy was performed on a donor animal, followed by a cold preservation (on ice) of the harvested kidney for a period of 5 hours. At the end of this period, the recipient rat underwent a bilateral nephrectomy, followed by transplantation of the cold-preserved kidney graft. The total warm ischemia time (including surgical procedure) was 30 minutes. QM5 was administered intravenously via the femoral vein, either to the donor animal prior to the kidney harvest ("pre"), or to the recipient animal 15 minutes ("post 15 min") or 4 hours (post 4 hrs) post-transplantation.

To assess the efficacy of QM5 siRNA in improvement of post-transplantation renal function, serum creatinine levels were measured on days 1, 2, and 7 post-transplantation in both warm and cold ischemia models.

In the warm ischemia experiments, serum creatinine levels in post-transplantation animals were lower in all QM5-treated groups compared to the control group, at all time points analyzed (Table 3 below); however, only at 24 hours post-transplantation were serum creatinine levels in all treatment groups statistically significantly lower than the control group. Group 3 ("post") and Group 4 ("pre-post") showed the lowest serum creatinine levels (1.11±0.68 mg/dL and 0.84±0.67 mg/dL, respectively) relative to the control group (2.36±0.99 mg/dL). No significant differences in the serum creatinine levels were found between siRNA treatment groups (adjusted p-value>0.90). These data demonstrated the ability of p53 siRNA to protect rat kidney from transplantation-related acute kidney injury associated with warm ischemia and reperfusion.

TABLE 3A

Mean serum creatinine values in warm ischemia model

| | | 24 hours | | | 48 hours | | | 168 hours | | Adjusted P-value (Tukey) | | |
|---|---|---|---|---|---|---|---|---|---|---|---|---|
| Group | N | Mean | Std | N | Mean | Std | N | Mean | Std | Pre | Pre-Post | Post |
| Control | 10 | 2.36 | 0.99 | 5 | 1.35 | 0.99 | 3 | 0.60 | 0.24 | 0.3575 | 0.1071 | 0.1890 |
| Pre Injection | 6 | 1.45 | 1.03 | 5 | 0.94 | 0.75 | 3 | 0.44 | 0.05 | | 0.9134 | 0.9654 |

TABLE 3A-continued

Mean serum creatinine values in warm ischemia model

| Group | 24 hours | | | 48 hours | | | 168 hours | | | Adjusted P-value (Tukey) | | |
|---|---|---|---|---|---|---|---|---|---|---|---|---|
| | N | Mean | Std | N | Mean | Std | N | Mean | Std | Pre | Pre-Post | Post |
| Pre-Post Injection | 7 | 0.84 | 0.67 | 4 | 0.61 | 0.17 | 3 | 0.28 | 0.05 | | | 0.9976 |
| Post Injection | 6 | 1.11 | 0.68 | 5 | 0.77 | 0.21 | 3 | 0.38 | 0.23 | | | |

An important time point is 24 hours when the acute kidney damage develops. Table 3 shows the adjusted p-values according to Tukey method for time point 24 hours.

TABLE 3B

Tukey adjusted P-value for 24 hour time point

| 24 hours | Pre Injection | Pre-Post Injection | Post Injection |
|---|---|---|---|
| Control | 0.0653 | 0.0034 | 0.0198 |
| Pre Injection | | 0.1703 | 0.4415 |
| Pre-Post Injection | | | 0.4415 |

In the cold ischemia experiments, serum creatinine levels were statistically significantly reduced in all siRNA-treated groups, at all experimental time points compared to PBS-treated control (Table 4). No significant differences were found between siRNA treatment groups themselves. Serum creatinine levels in the control animals remained elevated one week post-transplantation (mean creatinine 1.25±0.71 mg/dL), indicating the occurrence of kidney injury. QM5-treated animals demonstrated almost two-fold lower (nearly basal) serum creatinine levels one week post-transplantation (0.63±0.18; 0.64±0.17; 0.63±0.31 for "pre", "post" and "pre-post" groups, respectively), indicating the ability of QM5 to protect the kidney from DGF (delayed graft function) associated with cold and warm ischemia and subsequent reperfusion.

TABLE 4

Mean serum creatinine levels in cold ischemia model

| Group | Time N | 24 hours | | 48 hours | | 168 hours | |
|---|---|---|---|---|---|---|---|
| | | Mean | Std | Mean | | Mean | Std |
| Control | 6 | 1.88 | 0.76 | 1.45 | 1.27 | 1.25 | 0.71 |
| Pre_30 m | 6 | 1.12 | 0.32 | 0.97 | 0.39 | 0.63 | 0.18 |
| Pos_15 m | 5 | 0.92 | 0.27 | 0.70 | 0.29 | 0.64 | 0.17 |
| Post_4 h | 6 | 1.15 | 0.22 | 0.70 | 0.13 | 0.63 | 0.31 |

In conclusion, TP53-targeted siRNA protects rats from transplantation-associated acute kidney injury and from cold ischemia-associated delayed graft function. The maximum siRNA efficacy in preventing warm ischemia associated kidney dysfunction in transplantation model in rats was achieved when siRNA was administered (at a dose of 12 mg/kg) either to the recipient within hours post-transplantation, or both to donor within minutes pre harvest, and to recipient within hours post-transplantation. The difference between these two treatment regiments was not statistically significant. The maximum efficacy of QM5 in preventing cold ischemia-associated delayed graft function was achieved when siRNA was administered to the recipient as a single bolus intravenous injection (12 mg/kg) within minutes or hours post-transplantation. There was no statistically significant difference between these two treatment regiments.

For further elaboration on model systems which are used to test the compounds of the present invention, see International patent publication Nos. WO 06/023544A2, WO 2006/035434 and WO 2007/084684A2, co-assigned or assigned to the assignee of the present invention, which are hereby incorporated by reference in their entirety.

Example 12

Generation of Sequences for Active siRNA Compounds to the Pro-Apoptotic Genes and Production of the siRNAs Using proprietary algorithms and the known sequence of each pro-apoptotic gene, the sequences of potential siRNAs were generated. SEQ ID NOS:68-849 and 850-1691 set forth TP53 19-mer and 21-mer siRNAs, respectively, as 5'-3' sequences, which are prioritized based on their score in the proprietary algorithm as the best sequences for targeting the human gene expression. A list of preferred siRNA to HTRA2 is set forth in SEQ ID NOS:1692-2471. A list of preferred siRNA to KEAP1 is set forth in SEQ ID NOS:2472-3435. A list of preferred siRNA to SHC1-SHC is set forth in SEQ ID NOS:3436-4035. A list of preferred siRNA to ZNHIT1 is set forth in SEQ ID NOS:4036-4709. A list of preferred siRNA to LGALS3 is set forth in SEQ ID NOS:4710-5381. A list of preferred siRNA to HI95 is set forth in SEQ ID NOS:5382-6815.

The siRNAs used in the experiments described herein are all 19-mers, having alternating ribonucleotides modified in both the antisense and the sense strands of the compound. The modification is such that a 2'-O-methyl (Me) group is present on the first, third, fifth, seventh, ninth, eleventh, thirteenth, fifteenth, seventeenth and nineteenth nucleotide of the antisense strand, whereby the very same modification, i.e. a 2'-O-Me group, is present at the second, fourth, sixth, eighth, tenth, twelfth, fourteenth, sixteenth and eighteenth nucleotide of the sense strand. These particular siRNA compounds are also blunt ended and are non-phosphorylated at the termini; however, comparative experiments have shown that siRNA compounds phosphorylated at one or both of the 3'-termini have similar activity in vivo compared to the non-phosphorylated compounds.

It will be appreciated by a person skilled in the art that the above specific embodiments are illustrative and that the present invention is not limited by what has been particularly shown and described hereinabove. It is intended that modifications, permutations, combinations and sub-combinations fall within the true scope of this disclosure and appended claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08785408B2). An electronic copy of the "Sequence Listing" will also be available from the USPTO upon request and payment of the fee set forth in 37 CFR 1.19(b)(3).

What is claimed is:

1. A method of reducing Delayed Graft Function (DGF) in a recipient of a kidney transplant from a deceased donor, comprising only between 15 minutes and 4 hours following revascularization of the transplanted kidney, intravenously administering to the recipient, a composition which comprises a double-stranded RNA compound having the structure:

```
5' (N)_x-Z 3'    (antisense strand)
3' Z'-(N')_y 5'  (sense strand)
``` wherein each N and N' is a ribonucleotide which may be unmodified or modified in its sugar residue;
wherein each of (N)x and (N')y is an oligonucleotide in which each consecutive ribonucleotide is joined to the next ribonucleotide by a covalent bond and each of x and y is an integer between 18 and 40;
wherein in each of (N)x and (N')y the ribonucleotides alternate between modified ribonucleotides and unmodified ribonucleotides, each modified ribonucleotide being a 2'-O-methyl sugar modified ribonucleotide;
wherein each of Z and Z' may be present or absent, but if present is 1-5 deoxyribonucleotides covalently attached at the 3' terminus of the oligonucleotide in which it is present;
wherein the sequence of the antisense strand comprises the sequence 5' UGAAGGGUGAAAUAUUCUC 3' (SEQ ID NO:2) and the sequence of the sense strand comprises the sequence 5' GAGAAUAUUUCACCCUUCA 3' (SEQ ID NO:1); and
wherein the composition comprises an amount of the compound effective to down-regulate expression of a p53 gene, and thereby reduce Delayed Graft Function (DGF) in the recipient.

2. The method of claim 1, wherein the composition is administered as a single, slow intravenous push.

3. The method of claim 1, wherein x=y=19.

4. The method of claim 2, wherein the ribonucleotide at the 5' terminus and the ribonucleotide at the 3' terminus of the antisense strand are 2'-O-methyl modified in their sugar residues, and the ribonucleotide at the 5' terminus and the ribonucleotide at the 3' terminus of the sense strand are unmodified in their sugar residues; and wherein both of Z and Z' are absent.

5. The method of claim 1, wherein the antisense strand and the sense strand may be phosphorylated or non-phosphorylated at their 3' terminus or their 5' terminus or both.

6. The method of claim 1, wherein the DGF is cold ischemia-associated DGF.

7. The method of claim 1, wherein the amount of the double-stranded RNA compound is between 0.1 and 50 mg/kg body weight of the recipient.

8. The method of claim 7, wherein the amount of the double-stranded RNA compound is between 0.5 and 10 mg/kg body weight of the recipient.

9. A method of protecting a recipient of a kidney transplant from a deceased donor from Delayed Graft Function (DGF) comprising only between 15 minutes and 4 hours following revascularization of the transplanted kidney intravenously administering to the recipient a composition which comprises a double-stranded RNA compound having the structure:

```
5' UGAAGGGUGAAAUAUUCUC 3'  (antisense strand;
                            SEQ ID NO: 2)
3' ACUUCCCACUUUAUAAGAG 5'  (sense strand;
                            SEQ ID NO: 1)
``` wherein each of A, C, U and G is an unmodified ribonucleotide or a 2'-O-methyl sugar modified ribonucleotide and each consecutive ribonucleotide is joined to the next ribonucleotide by a covalent bond;
wherein in the antisense strand the first, third, fifth, seventh, ninth, eleventh, thirteenth, fifteenth, seventeenth and nineteenth ribonucleotide are 2'-O-methyl sugar modified ribonucleotides;
wherein in the sense strand the second, fourth, sixth, eighth, tenth, twelfth, fourteenth, sixteenth and eighteenth ribonucleotide are 2'-O-methyl sugar modified ribonucleotides; and
wherein the composition comprises an amount of the compound effective to down-regulate expression of a p53 gene, and thereby protect the recipient from Delayed Graft Function (DGF).

10. The method of claim 9, wherein the DGF is cold ischemia-associated DGF.

11. The method of claim 9, wherein the donor died from brain or cardiac death.

12. The method of claim 9, wherein the amount of the double-stranded RNA compound is between 0.1 and 50 mg/kg body weight of the recipient.

13. The method of claim 12, wherein the amount of the double-stranded RNA compound is between 0.5 and 10 mg/kg body weight of the recipient.

14. The method of claim 1, wherein the donor died from brain or cardiac death.

15. The method of claim 1, wherein the composition is administered as a single administration.

16. The method of claim 9, wherein both the antisense strand and the sense strand are non-phosphorylated at the 3' termini and the 5' termini.

17. The method of claim 9, wherein the composition is administered as a single administration.

18. The method of claim 17, wherein the composition is administered as a single, slow intravenous push.

19. The method of claim 1, wherein the amount of the double-stranded RNA compound is 10 mg/kg body weight of the recipient.

20. The method of claim 9, wherein the amount of the double-stranded RNA compound is 10 mg/kg body weight of the recipient.

* * * * *